(12) United States Patent
Whayne

(10) Patent No.: US 6,858,035 B2
(45) Date of Patent: Feb. 22, 2005

(54) DISTAL ANASTOMOSIS SYSTEM

(75) Inventor: James G. Whayne, Chapel Hill, NC (US)

(73) Assignee: Converge Medical, Inc., Sunnyvale, CA (US)

( * ) Notice: Subject to any disclaimer, the term of this patent is extended or adjusted under 35 U.S.C. 154(b) by 373 days.

(21) Appl. No.: 09/991,469

(22) Filed: Nov. 21, 2001

(65) Prior Publication Data

US 2003/0009183 A1 Jan. 9, 2003

Related U.S. Application Data

(63) Continuation-in-part of application No. 09/899,346, filed on Jul. 5, 2001.

(51) Int. Cl.⁷ .............................................. A61B 17/08
(52) U.S. Cl. ...................................... 606/153; 606/151
(58) Field of Search ................................. 606/151, 153, 606/155, 213, 215, 219–221

(56) References Cited

U.S. PATENT DOCUMENTS

| | | |
|---|---|---|
| 4,214,587 A | 7/1980 | Sakura, Jr. |
| 4,366,819 A | 1/1983 | Kaster |
| 4,368,736 A | 1/1983 | Kaster |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |
| 4,787,386 A | 11/1988 | Walsh et al. |
| 4,917,087 A | 4/1990 | Walsh et al. |
| 4,917,090 A | 4/1990 | Berggren et al. |
| 4,917,091 A | 4/1990 | Berggren et al. |
| 4,950,227 A | 8/1990 | Savin et al. |
| 5,067,957 A | 11/1991 | Jervis |
| 5,078,736 A | 1/1992 | Behl |
| 5,156,613 A | 10/1992 | Sawyer |

(List continued on next page.)

FOREIGN PATENT DOCUMENTS

| | | |
|---|---|---|
| EP | 824 901 A2 A3 | 2/1998 |
| EP | 894 475 A1 | 2/1999 |
| WO | WO 96/22745 A1 | 8/1996 |
| WO | WO 97/13463 A1 | 4/1997 |
| WO | WO 97/13471 A1 | 4/1997 |
| WO | WO 97/16122 A1 | 5/1997 |
| WO | WO 97/27893 A1 | 8/1997 |
| WO | WO 97/27897 A1 | 8/1997 |
| WO | WO 97/27898 A1 | 8/1997 |
| WO | WO 97/31575 A1 | 9/1997 |

(List continued on next page.)

OTHER PUBLICATIONS

U.S. Appl. No. 09/329,503, filed Jun. 10, 1999, Fleischman et al.
U.S. Appl. No. 09/329,504, filed Jun. 10, 1999, Fleischman et al.
U.S. Appl. No. 09/329,658, filed Jun. 10, 1999, Fleischman et al.
U.S. Appl. No. 09/415,776, filed Oct. 8, 1999, Fleischman et al.
U.S. Appl. No. 09/654,216, filed Sep. 1, 2000, Fleischman et al.

(List continued on next page.)

Primary Examiner—Julian W. Woo
(74) Attorney, Agent, or Firm—Carol M. LaSalle; Bozicevic, Field & Francis LLP

(57) ABSTRACT

Distal anastomosis devices and associated methodology are provided for producing an anastomosis at a graft/coronary artery junction.

34 Claims, 20 Drawing Sheets

U.S. PATENT DOCUMENTS

| | | |
|---|---|---|
| 5,190,546 A | 3/1993 | Jervis |
| 5,234,447 A | 8/1993 | Kaster et al. |
| 5,391,156 A | 2/1995 | Hildwein et al. |
| 5,405,322 A | 4/1995 | Lennox et al. |
| 5,443,497 A | 8/1995 | Venbrux |
| 5,503,635 A | 4/1996 | Sauer et al. |
| 5,571,167 A | 11/1996 | Maginot |
| 5,591,226 A | 1/1997 | Trerotola et al. |
| 5,597,378 A | 1/1997 | Jervis |
| 5,628,784 A | 5/1997 | Strecker |
| 5,657,429 A | 8/1997 | Wang et al. |
| 5,665,117 A | 9/1997 | Rhodes |
| 5,669,934 A | 9/1997 | Sawyer |
| 5,676,670 A | 10/1997 | Kim |
| 5,690,675 A | 11/1997 | Sawyer et al. |
| 5,695,504 A | 12/1997 | Gifford, III et al. |
| 5,697,968 A | 12/1997 | Rogers et al. |
| 5,702,418 A | 12/1997 | Ravenscroft |
| 5,713,917 A | 2/1998 | Leonhardt et al. |
| 5,720,755 A | 2/1998 | Dakov |
| 5,725,544 A | 3/1998 | Rygaard |
| 5,728,133 A | 3/1998 | Kontos |
| 5,749,375 A | 5/1998 | Maginot |
| 5,749,895 A | 5/1998 | Sawyer et al. |
| 5,755,775 A | 5/1998 | Trerotola et al. |
| 5,755,778 A | 5/1998 | Kleshinski |
| 5,762,458 A | 6/1998 | Wang et al. |
| 5,779,718 A | 7/1998 | Green et al. |
| 5,797,920 A | 8/1998 | Kim |
| 5,797,934 A | 8/1998 | Rygaard |
| 5,810,884 A | 9/1998 | Kim |
| 5,814,005 A | 9/1998 | Barra et al. |
| 5,824,015 A | 10/1998 | Sawyer |
| 5,861,003 A | 1/1999 | Latson et al. |
| 5,868,759 A | 2/1999 | Peyser et al. |
| 5,868,761 A | 2/1999 | Nicholas et al. |
| 5,868,770 A | 2/1999 | Rygaard |
| 5,871,536 A | 2/1999 | Lazarus |
| 5,893,886 A | 4/1999 | Zegdi et al. |
| 5,931,842 A | 8/1999 | Goldsteen et al. |
| 5,934,286 A | 8/1999 | Maginot |
| 5,938,672 A | 8/1999 | Nash |
| 5,938,696 A | 8/1999 | Goicoechea et al. |
| 5,944,019 A | 8/1999 | Knudson et al. |
| 5,944,730 A | 8/1999 | Nobles et al. |
| 5,944,738 A | 8/1999 | Amplatz et al. |
| 5,944,750 A | 8/1999 | Tanner et al. |
| 5,954,735 A | 9/1999 | Rygaard |
| 5,957,940 A | 9/1999 | Tanner et al. |
| 5,964,782 A | 10/1999 | Lafontaine et al. |
| 5,968,053 A | 10/1999 | Revelas |
| 5,968,089 A | 10/1999 | Krajicek |
| 5,968,090 A | 10/1999 | Ratcliff et al. |
| 5,972,017 A | 10/1999 | Berg et al. |
| 5,972,023 A | 10/1999 | Tanner et al. |
| 5,976,178 A | 11/1999 | Goldsteen et al. |
| 5,979,455 A | 11/1999 | Maginot |
| 5,984,955 A | 11/1999 | Wisselink |
| 5,989,276 A | 11/1999 | Houser et al. |
| 5,989,287 A | 11/1999 | Yang et al. |
| 5,993,468 A | 11/1999 | Rygaard |
| 6,001,124 A | 12/1999 | Bachinski |
| 6,004,347 A | 12/1999 | McNamara et al. |
| 6,007,576 A | 12/1999 | McClellan |
| 6,010,529 A | 1/2000 | Herweck et al. |
| 6,017,352 A | 1/2000 | Nash et al. |
| 6,019,788 A | 2/2000 | Butters et al. |
| 6,030,370 A | 2/2000 | Kupka et al. |
| 6,030,392 A | 2/2000 | Dakov |
| 6,030,395 A | 2/2000 | Nash et al. |
| 6,036,702 A | 3/2000 | Bachinski et al. |
| 6,036,703 A | 3/2000 | Evans et al. |
| 6,036,705 A | 3/2000 | Nash et al. |
| 6,048,362 A | 4/2000 | Berg |
| 6,056,762 A | 5/2000 | Nash et al. |
| 6,059,824 A | 5/2000 | Taheri |
| 6,063,114 A | 5/2000 | Nash et al. |
| 6,068,654 A | 5/2000 | Berg et al. |
| 6,071,305 A | 6/2000 | Brown et al. |
| 6,074,416 A | 6/2000 | Berg et al. |
| 6,113,612 A | 9/2000 | Swanson et al. |
| 6,117,147 A | 9/2000 | Simpson et al. |
| 6,120,432 A | 9/2000 | Sullivan et al. |
| 6,149,681 A | 11/2000 | Houser et al. |
| 6,152,937 A | 11/2000 | Peterson et al. |
| 6,293,955 B1 | 9/2001 | Houser et al. |
| 6,352,543 B1 | 3/2002 | Cole |
| 6,419,681 B1 | 7/2002 | Vargas et al. |
| 6,428,550 B1 | 8/2002 | Vargas et al. |
| 6,443,965 B1 | 9/2002 | Gifford, III et al. |

FOREIGN PATENT DOCUMENTS

| | | |
|---|---|---|
| WO | WO 97/40754 A1 | 11/1997 |
| WO | WO 97/43961 A1 | 11/1997 |
| WO | WO 98/03118 A1 | 1/1998 |
| WO | WO 98/06350 A1 | 2/1998 |
| WO | WO 98/07399 A1 | 2/1998 |
| WO | WO 98/08456 A1 | 3/1998 |
| WO | WO 98/19608 A1 | 5/1998 |
| WO | WO 98/19618 A1 | 5/1998 |
| WO | WO 98/19625 A2 | 5/1998 |
| WO | WO 98/19629 A2 | 5/1998 |
| WO | WO 98/19630 A2 | 5/1998 |
| WO | WO 98/19631 A1 | 5/1998 |
| WO | WO 98/19632 A1 | 5/1998 |
| WO | WO 98/19634 A2 | 5/1998 |
| WO | WO 98/19635 A1 | 5/1998 |
| WO | WO 98/19636 A2 | 5/1998 |
| WO | WO 98/19732 A1 | 5/1998 |
| WO | WO 98/38939 A1 | 9/1998 |
| WO | WO 98/38941 A1 | 9/1998 |
| WO | WO 98/40036 A1 | 9/1998 |
| WO | WO 98/42262 A1 | 10/1998 |
| WO | WO 98/52474 A1 | 11/1998 |
| WO | WO 98/55027 A2 | 12/1998 |
| WO | WO 98/57590 A1 | 12/1998 |
| WO | WO 98/57591 A1 | 12/1998 |
| WO | WO 98/57592 A1 | 12/1998 |
| WO | WO 99/00055 A2 | 1/1999 |
| WO | WO 99/18887 A1 | 4/1999 |
| WO | WO 99/38454 A2 | 8/1999 |
| WO | WO 99/45852 A2 | 9/1999 |
| WO | WO 99/48427 A1 | 9/1999 |
| WO | WO 99/62408 A1 | 12/1999 |
| WO | WO 99/62415 A1 | 12/1999 |
| WO | WO 99/63910 A1 | 12/1999 |
| WO | WO 99/65409 A1 | 12/1999 |
| WO | WO 00/09040 A1 | 2/2000 |
| WO | WO 00/15144 A1 | 3/2000 |
| WO | WO 00/2731 A1 | 5/2000 |
| WO | WO 00/24339 A1 | 5/2000 |
| WO | WO 00/27313 A2 | 5/2000 |
| WO | WO 00/40176 A1 | 7/2000 |
| WO | WO 00/53104 A1 | 9/2000 |
| WO | WO 01/41653 A2 | 6/2001 |

OTHER PUBLICATIONS

U.S. Appl. No. 09/730,366, filed Dec. 5, 2000, Fleischman et al.

U.S. Appl. No. 09/770,560, filed Jan. 26, 2001, Whayne.

U.S. Appl. No. 60/227,680, filed Aug. 24, 2000, Whayne et al.

U.S. Appl. No. 60/231,368, filed Sep. 8, 2000, Davidson et al.

Cragg, A.H. et al. (1982). "Endovascular Diathermic Vessel Occlusion," *Radiology* 144:303–308.

Gorisch, W. et al. (1982). "Heat–Induced Contraction of Blood Vessels," *Lasers in Surgery and Medicine* 2:1–13.

Heijmen, R.H. et al., (1999). "A Novel One–Shot Anastomotic Stapler Prototype for Coronary Bypass Grafting on the Bearing Heart: Feasibility in the Pig," *Journal of Thoracic and Cardiovascular Surgery* 117(1): 117–125.

Yusuf, S.W. et al. (1994). "Transfermoral Endolumimal Repair of Abdominal Aortic Aneurysm with Bifuricated Graft," *Lancet* 344(8923): 650–651.

DISTAL ANASTOMOSIS SYSTEM

CROSS-REFERENCE TO RELATED APPLICATIONS

This application is a continuation-in-part of U.S. patent application Ser. No. 09/899,346 entitled "Distal Anastomosis System" filed Jul. 5, 2001, which is incorporated herein by reference in its entirety.

FIELD OF THE INVENTION

This relates to producing end-to-side anastomoses, particularly in communication with coronary arteries. Accordingly, distal anastomosis fittings and associated devices are disclosed.

BACKGROUND OF THE INVENTION

Current techniques for producing anastomoses during coronary artery bypass grafting procedures involve placing a patient on cardiopulmonary bypass support, arresting the heart, and interrupting blood flow in order to suture, clip or staple a bypass graft to the coronary artery and aorta. However, cardiopulmonary bypass support is associated with substantial morbidity and mortality.

This invention provides devices and methods to avoid bypass support by allowing for positioning and securing bypass grafts at host vessel locations without having to stop or re-route blood flow. In addition, this invention mitigates risks associated with suturing, clipping or stapling the bypass graft to a host vessel. This may be accomplished, in part, by features adapted to avoid bleeding at graft attachment sites and avoiding collapse of a host vessel around the incision point. Further, the invention optionally provides features to improve blood flow within a graft and increase the patency of a graft.

In performing cardiac bypass surgery, anastomosis sites are typically provided at a proximal site along a patient's aorta, and a distal site along a coronary artery beyond a partial or complete occlusion. Producing an effective anastomosis along a coronary artery is particularly challenging. The outer diameter of a coronary artery where a distal anastomosis may be needed can range from between about 1 mm to about 4 mm in size. By way of comparison, the outer diameter of the aorta where a proximal anastomosis may be located ranges between about 20 mm and about 50 mm in size.

The relatively small size of the site for a distal anastomosis translates to greater difficulty in a number of ways. Basic surgical challenges are encountered in dealing with the smaller vasculature. Further, an interface issue is introduced. Often, particularly for connection with the smaller coronary arteries, a graft conduit will have a larger diameter than the host vessel. This may be due to the need for a larger diameter conduit to carry adequate blood flow or the result of using a saphenous vein which must be inverted for use due to its valving, thereby orienting the larger end of the graft toward the distal site. For whatever reason, the mismatch in size in joining the graft to the coronary artery must be dealt with. The present invention is adapted to handle these issues as well as others as may be apparent to those with skill in the art. The distal-type connectors described herein may be employed with precision and speed, resulting in treatment efficacy not heretofore possible.

SUMMARY OF THE INVENTION

The invention includes various improvements in end-side anastomosis systems. Particularly, connectors for producing distal anatomoses are described. They each include a fitting comprising a rear section with a segment that deflectable about a hinge section to allow for placement and securing the device. Curvilinear side and forward-facing portions are preferred. Most preferably, these portions are configured to conform to the shape of a host vessel. Such a fitting may alone serve as a connector between a host vessel and a graft. Alternately, the connector may comprise a fitting in combination with a collar adapted to secure a graft to the fitting.

Various features for improving the deployability of a connector, hemostasis at the connector and blood flow through a graft may be provided by the invention. Further, various tools for use in preparing for and creating an end-side anastomosis may comprise part of the invention.

While connectors and deployment devices according to the present invention are preferably used in coronary artery bypass grafting procedures, particularly at a distal location, it is to be understood that the systems described herein may be used for purposes other than creating distal anastomoses. The systems may also be used to produce anastomoses between bypass grafts and host vessels to treat other occlusions, vascular abnormalities such as stenoses, thromboses, aneurysms, fistulas and indications requiring a bypass graft. The system of the present invention is also useful in bypassing stented vessels that have restenosed, and saphenous vein bypass grafts that have thrombosed or stenosed. Further, the invention may have other applications, such as producing arterial to venous shunts for hemodialysis, bypassing lesions and scar tissue located in the fallopian tubes causing infertility, attaching the ureter to the kidneys during transplants, and treating gastrointestinal defects (e.g., occlusions, ulcers, obstructions, etc.).

The present invention variously includes the devices as well as the methodology disclosed. Furthermore, it is contemplated that subcombinations of features, especially of the connector features disclosed, comprise aspects of the invention.

BRIEF DESCRIPTION OF THE DRAWINGS

Each of the following figures diagrammatically illustrates aspects of the present invention. The illustrations provide examples of the invention described herein. Like elements in the various figures often are represented by identical numbering. For the sake of clarity, some such numbering may be omitted.

DETAILED DESCRIPTION OF THE INVENTION

The variations of the invention discussed herein are applicable to robotic surgery and less invasive (i.e., minimally invasive) surgery involving a thoracostomy or mini median stemotomy to access the anastomosis site as well as the surgical approaches, such as that described below. As noted above, the present invention includes variations of anastomosis connectors. Anastomosis connectors, tools and associated methodology for producing proximal anastomoses are described variously in U.S. and foreign patent and applications entitled, "Percutaneous Bypass Graft and Securing System", U.S. Pat. No. 5,989,276; "Percutaneous Bypass Graft and Securing System", U.S. patent application Ser. No. 09/415,776; Percutaneous Bypass Graft Securing System", PCT Publication No. WO 98/19625; "Sutureless Anastomosis Systems", U.S. patent application Ser. No. 09/329,503; "Sutureless Anastomosis Systems", PCT Publication No. WO 99/65409; "Thermal Securing Anastomosis Systems" U.S. patent application Ser. No. 09/329,504; "Thermal Securing Anastomosis Systems", PCT Publication No. WO 99/63910; "Aortic Aneurysm Treatment Sytems", U.S. patent application Ser. No. 09/329,658; "Aortic Aneurysm Treatment Systems", PCT Publication No. WO 00/15144; "Additional Sutureless Anastomosis Embodiments", U.S. patent application Ser. No. 09/654,216; "Improved Anastomosis Systems", U.S. patent application Ser. No. 09/730,366; "End-Side Anastomosis Systems", PCT Publicatioin No. WO 01/416653; "Advanced Anastomosis Systems (II)", U.S. patent application Ser. No. 09/770,560; "Pre-Ionization of Mammalian Implants", U.S. Provisional Patent Application Ser. No. 60/231,368; and "Sutureless Anastomosis System Deployment Concepts", U.S. patent application Ser. No. 60/227,680 and applications and patents claiming benefit hereto, all of which are incorporated herein by reference in their entirety and all commonly owned by Converge Medical, Inc.

Figure 1:
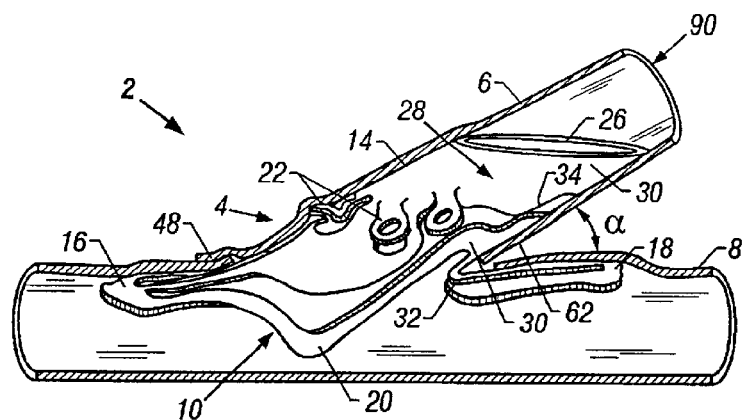
FIG. 1 shows a side view of an installed connector according to the present invention.
Figure 2:
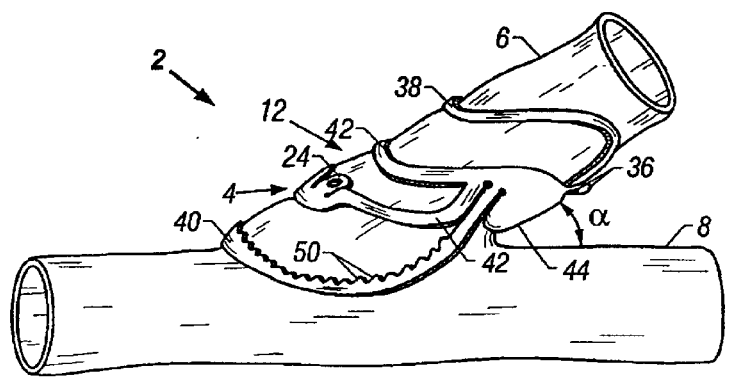
FIG. 2 shows a side view of another installed connector according to the present invention, this connector including a collar for securing the graft shown to a fitting.

FIGS. 1 and 2 show distal anastomoses (2) formed by connectors (4) according to the present invention. Each connector (4) attaches a graft (6) to a host vessel (8). In this case, the host vessel is a coronary artery. Graft (6) preferably comprises a saphenous vein, though a synthetic graft (such as one made of expanded PTFE) can be utilized. FIG. 1 shows a connector provided by a fitting (10) only. The connector in FIG. 2 includes a fitting (hidden) as well as a collar (12).

Referring to FIG. 1, various features of fitting (10) may be observed. First, it is noted that fitting and attached graft (6) are preferably configured so its base or body (14) is at an angle α with respect to host vessel (8). Connectors (2) are shown at approximately a 30° angle. Preferred angles for distal anastomosis range from about 20° to about 70°. A more preferable range is from about 30° to about 60°. Most preferably, they are between about 30° and about 45°. The angle helps maintain hemostasis and proper blood flow once the anastomosis is created and retracted organs and tissue bear upon the site. Pressure created by such action will not dislodge connector (4) or kink or collapse graft (6) since the angle allows graft (6) to leave the connector (4) and lie substantially in line with the heart. In addition to improving blood-carry capability of the conduit in assuring stability of the connector, including some angle in the connector enables the manner of deployment taught below.

Fitting (10) includes at least a front or leading segment (16) and a rear or trailing segment (18). When situated to form an anastomosis, these segments lie approximately in line with host vessel (8). So-placed, they prevent removal of the connector from the host vessel. Optional lateral or side portions (20) may also aid in this regard. This is especially the case in forming an anastomosis with a very small diameter vessel (such as a 1 to 4 mm diameter coronary artery). Furthermore, lateral portions (20) may assist in providing a physical barrier to leakage. This may be true irrespective of the size of host vessel (8). The use of one or more lateral portions (20) on each side of fitting (10) may also provide a smooth transition between the leading and trailing portions of fitting (10) to help moderate or alleviate trauma to the interior of the host vessel (8). Also, lateral portions (20) are also preferably configured such that they allow fitting (10) to flex with the wall of host vessel (8). For instance, as the heart pumps blood through the vascular system, host vessel (8) may move or undulate with the pumping action of the heart; accordingly, fitting (10) may also move or flex in part by lateral portions (20) with the natural motion of the vessel (8). The front or leading segment (16) may have a rounded toe-like configuration to also facilitate entry of the fitting (10) into the opening within the wall of the host vessel (8).

Figure 3A:
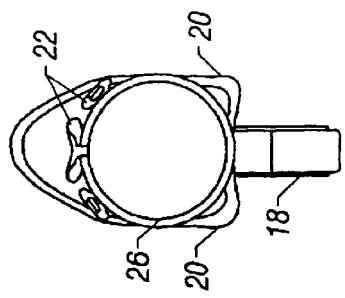
FIGS. 3A and 3B show side and end views of a fitting as may be used according to that shown in FIGS. 1 and 2.

A lateral portion may be provided integrally with a form providing at least part of leading segment (16). Alternately, or additionally (as shown in FIG. 3A), lateral portions (20) may be provided in discrete form. Especially when pushed toward the rear of fitting (10), such a member will work in conjunction with rear segment (18) to maintain hemostasis at connector (4). Furthermore, lateral portions (20) not only provide a smooth transition extending between the leading and trailing portions of fitting (10), but they are configured to minimize the contact area with the inner surface of host vessel (8). The total contact area in which fitting (10)

engages the host vessel (8) inner wall is preferably no greater than 5% to 35% of the inner surface area of fitting (10) against host vessel (8).

Additional optional features of fitting (10) include tabs (22) to assist in securing graft (6) and/or optional collar (12). Such tabs may be oriented to grip graft (6) as shown in FIG. 1. One or more tabs may also be adapted to form a locking interface with one or more complementary tabs (24) optionally included in collar (12). Also, the height or amount of material incorporated in the base of the fitting may be varied. In order to utilize as little material as possible to join the various segments, base (14) may be provided by a narrow band of material as shown in FIGS. 3A, 16A–16C or otherwise. To achieve proper relative placement of these features, base (14) may be curved or undulate.

Figure 3B:
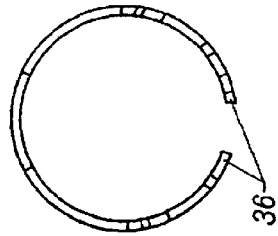

As shown in FIG. 3B, the connector opening (26) may have a circular bore; alternately, it may be ovalized. Configuring fitting (10) with an ovalized opening (26) may be useful in providing an interface at a smaller host vessel. It provides a manner in which to account for the size difference between the vessel and what is often a larger opening of the graft by. The ovalization increases the available perimeter to accommodate a host vessel without increasing the lateral size of the connector. Instead, a connector is lengthened. This will usually be an acceptable alteration in connector geometry since only the size of the arteriotomy made in the host vessel need be lengthened to fit the connector in place.

Features that are required of fitting (10), in addition to the basic leading and trailing segment configuration, are found in connection with a hinge section (28). Hinge section (28) may be provided in a number of configurations. However, the configurations serve the same purpose. Each of the variations shown and described allow rear segment (18) to be displaced sufficiently to clear the host vessel wall for insertion of the connector into the host vessel by significant torsional deflection of areas between rear segment (18) and fitting body (14). In the fitting variations shown in FIGS. 1 and 3A and 3B, a pair of torsion sections (30) are presented on each side of rear segment (18). In the variation in FIGS. 16A–16C, hinge section (28) includes only one torsion section (30) on each side of rear segment (18).

To displace rear segment (18) sufficiently, the primary deflection does not occur at bend (32) as with the distal connectors described in U.S. and foreign patents and applications entitled, "Improved Anastomosis Systems", U.S. patent application Ser. No. 09/730,366; "End-Side Anastomosis Systems", PCX Publication No. WO 01/41653; "Advanced Anastomosis Systems (II)" U.S. patent application Ser. No. 09/770,560. Rather, rotation about torsional sections accounts for at least half, if not most or substantially all of the displacement required of rear segment (18). In the variation of the fitting shown in FIGS. 16A–16C, rotation of rear segment (18) occurs about the pair of torsional members (30), whereas in the variations in FIGS. 1 and 3A and 3B, the rotation that occurs is shared between two pair of torsional sections.

Such dual action provides for certain advantages notable in the variations shown in FIGS. 1, 3A and 3B. Namely, upon forward deflection of rear segment (18), the lateral portions connected to torsional sections are caused to be drawn or flexed inward. This action facilitates introduction of connector (4) into host vessel (8) by clearing portions that could otherwise interfere with entry.

In the variation of the invention shown in FIG. 1, it may be observed that the torsional regions may be provided either by a wire segment or simply by a portion of the base of the fitting reduced to a relatively narrow section by a feature such as a cut, break, groove or slit (34) in the material. In the variation shown in FIGS. 16A–16C, no marked reduction in size relative to another portion of the fitting base is apparent.

Figure 16A:
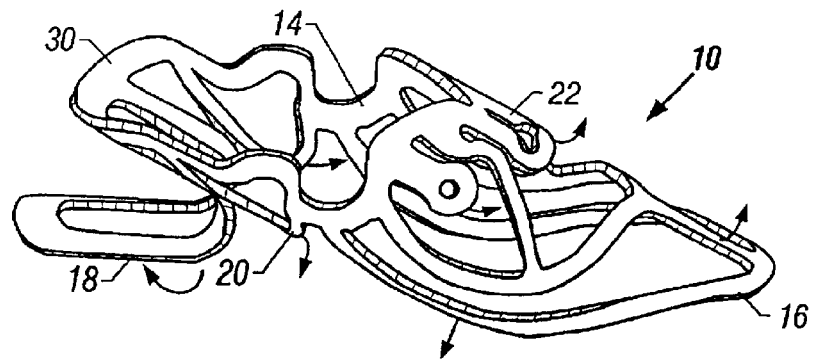
FIGS. 16A–16C show oblique, top and bottom views of a connector fitting according to the present invention at an intermediate stage of manufacture.
Figure 16B:
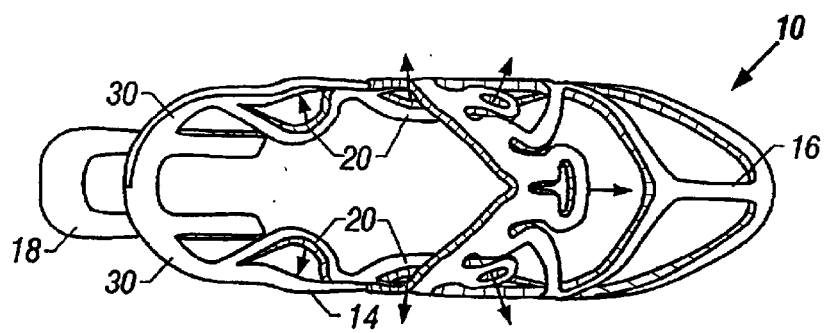
Figure 16C:
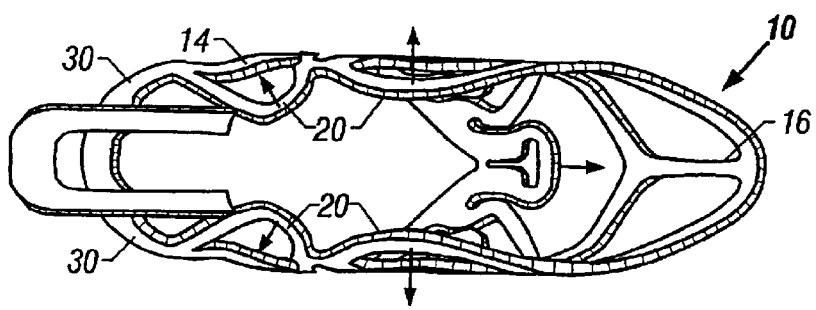

For fittings configured similarly to that in FIGS. 16A–16C, it is also noted that rotation of members (30) in deflecting rear section forward will cause lateral portions (20) to be drawn inward to some extent. However, the amount of inward deflection will be less relative to the variations of the fitting shown in FIGS. 1 and 3A and 3B where lateral portions (20) are directly connected to torsional sections.

Figure 4A:
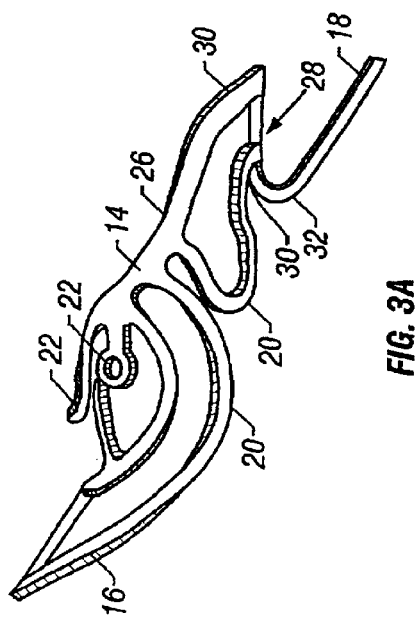
FIGS. 4A and 4B show side and end views of a collar as may be used according to that shown in FIG. 2.
Figure 4B:
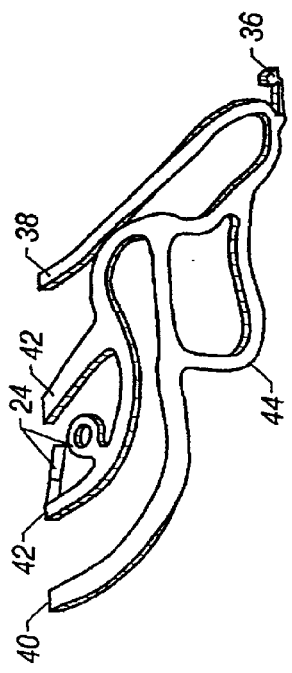

Turning now to the features of collar (12), FIGS. 2, 4A and 4B illustrate desirable features of this part of connector (4). A primary purpose of collar (12) is to secure graft (6) to fitting (4). As noted above, optional collar tab(s) (24) may assist in this regard by interfacing with optional fitting tab(s) (22). Also, collar (12) may be made to be resiliently biased against graft (6) to hold it to fitting (4). Further, interlocking members (36) may be provided to ensure a secure fit of collar (12) about fitting (6). One or more of these interlocking members may take the form of a hook as shown in FIG. 4A. Provision of a latching mechanism (36) also eliminates any perceived need to use a locking member such as a retaining clip, suture, implantable clips, staples, or other device that might be desired to ensure graft (6) is secured to fitting (4).

Collar (12) may comprise at least a proximal band (38) and a distal band (40). One or more intermediate bands or band segments (42) may also be provided, upon which optional tabs (24) may be mounted.

In the variations of connector (12) shown in FIGS. 2, 4A and 4B, lateral portions (44) are also provided. Preferably, they overlap or interface with corresponding lateral features (20) of a complimentary fitting (10) to form a complete seal at an anastomosis site. Likewise, the shape of the bore of the collar as shown in FIG. 4B should complement that of the fitting. In instances where the fitting has a circular bore (26) as shown in FIG. 3B, at least a mating portion of collar (12) should be substantially circular as well. In instances where fitting bore (26) is ovalized, a corresponding shape should be utilized in collar (12).

Figure 12A:
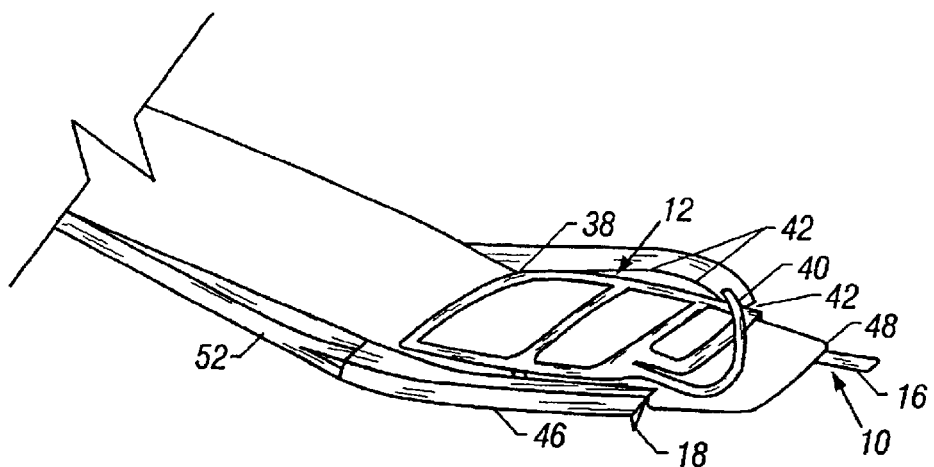
FIG. 12A shows a connector ready for deployment, restrained in customized Rongeur clamp.
Figure 12B:
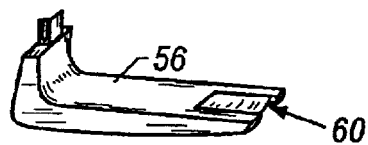
FIG. 12B shows an oblique view of the top of a lower section of the instrument in FIG. 12A.
Figure 12C:
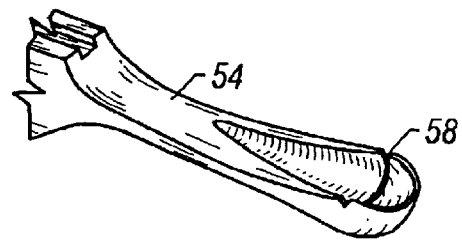
FIG. 12C shows an oblique view of the underside of an upper section of the instrument in FIG. 12A.

FIG. 12A shows another collar (12) in combination with a fitting (10). In this collar, the band portions attach to opposite rib segments (46) at the rear of collar (12). No lateral portions as shown in the above-referenced figures are included in this type of fitting. This type of collar functions well with fitting like those shown in FIG. 1, that only include a pair of lateral portions (20), instead of two pair like the connectors shown in FIGS. 3A, and 16A–16C.

In addition to the collar bands forming part of a structure to help secure graft (6) to fitting (4), at least the proximal and distal bands—(38) and (40)—may provide additional utility. Proximal band (38), possibly in connection with adjacent portions of collar (12) may be configured to provide a graft/connector transition allowing for greater blood flow and/or preservation of the character of a graft, particularly a saphenous vein graft.

When exposed to arterial blood pressure, saphenous veins may balloon, producing turbulent flow adjacent to the anastomosis site. This may lead to hyperplasia or other unwanted physiologic abnormalities. This tendency is exacerbated by any abrupt transition in stiffness along its length. Avoidance of ballooning mitigates the physiologic risks and also ensures a better flow profile within graft (6).

To reduce the tendency for a saphenous vein graft to balloon, proximal band (38) may be of a lower stiffness than adjacent bands. It is also preferable that it have a curvilinear shape like that depicted in FIGS. 2 and 4A. Alternately, it may follow a substantially straight line as viewed from the side as depicted in FIG. 12A. Either way, it is preferred that band (38) not run a circumference perpendicular to graft (4). By setting band (38) askew or by utilizing an undulating form, graft (4) does not suddenly lack support about an area in which it may easily balloon.

As for distal band (40), it may be used to help form a hemostatic seal between host vessel (8) and graft (6) and/or connector fitting (10). Preferably, band (40) is designed to bear down upon a toe portion (48) of graft (6) once inserted into a host vessel (8). Also, it may be set to bridge any gap between graft (6) and host vessel (8). Either way, band (40) should grip graft (6) to ensure its proper location. Such interaction may be aided by the inclusion of undulating or serrated gripping features (50) in distal band (40).

In order to insert connector (4) to complete an anastomosis, it is preferred that distal band (40) be flexible. In inserting a connector according to the present invention including a fitting (10) and collar (12), it is preferably manipulated as shown in FIG. 12A. Here, a modified Rongeur clamp (52) is shown retracting band (40) and advancing distal segment (18) to prepare the connector for insertion into an opening in a coronary artery or other appropriate site. Instrument (52) includes an upper finger (54) and a lower finger (56), each with relieved interface sections (58) and (60) to accommodate band (40) and rear segment (18), respectively. Rear segment (18) extends beyond lower finger (56) to allow visualization to assist in insertion within host vessel (8).

Whether prepared in connection with a collar or not, connector (4) is preferably installed at an anastomosis site as shown in FIG. 1. Here, it may be observed that graft toe (48) preferably overlaps host vessel (8). A heel portion (62) may abut, overlap host vessel (8) or leave a slight gap. When a connector is provided with a collar (12), the visible result will resemble that in FIG. 2. Still, the preferred relation of graft (6) to host vessel (8) remains similar to that shown in FIG. 1, depending on the fitting configuration selected.

Figure 5A:
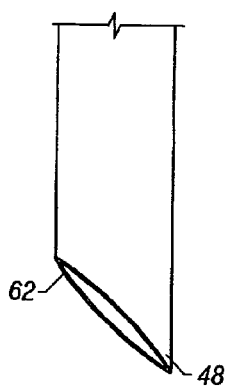
FIGS. 5A–5C show side views of graft vessels as they may be prepared.
Figure 5B:
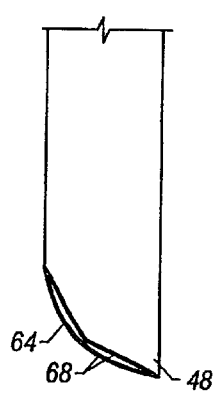
Figure 5C:
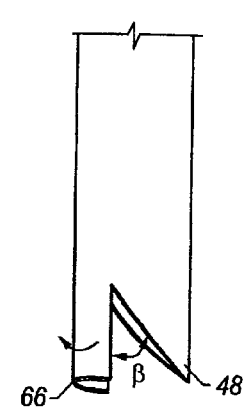

FIGS. 5A–5C, further illustrate graft preparation configurations. Graft (6) shown in FIG. 5A is configured like that shown in FIG. 1. Graft (6) shown in FIG. 5B differs by the inclusion of an "open" heal section (64); that in FIG. 5C has "high" heel section (66). The open-heel configuration provides for graft side extensions (68) offering additional graft material to overlap a host vessel upon connector insertion. The high-heel configuration also provides additional graft material to overlap a host vessel upon connector insertion. By flexing heel (66) outward to form an increased angle, β, heel (66) it is able to overlap the host vessel above at least a portion of rear segment (18) upon connector (4) insertion.

Figure 6A:
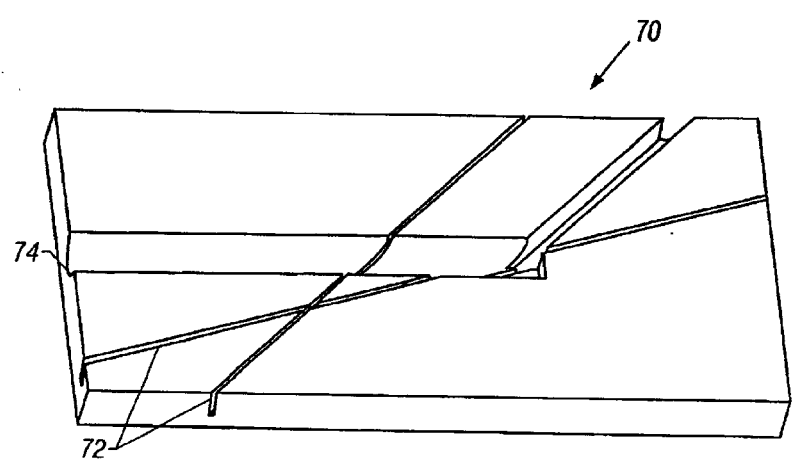
FIG. 6A shows an oblique view of a guide tool for preparing a graft vessel.
Figure 6B:
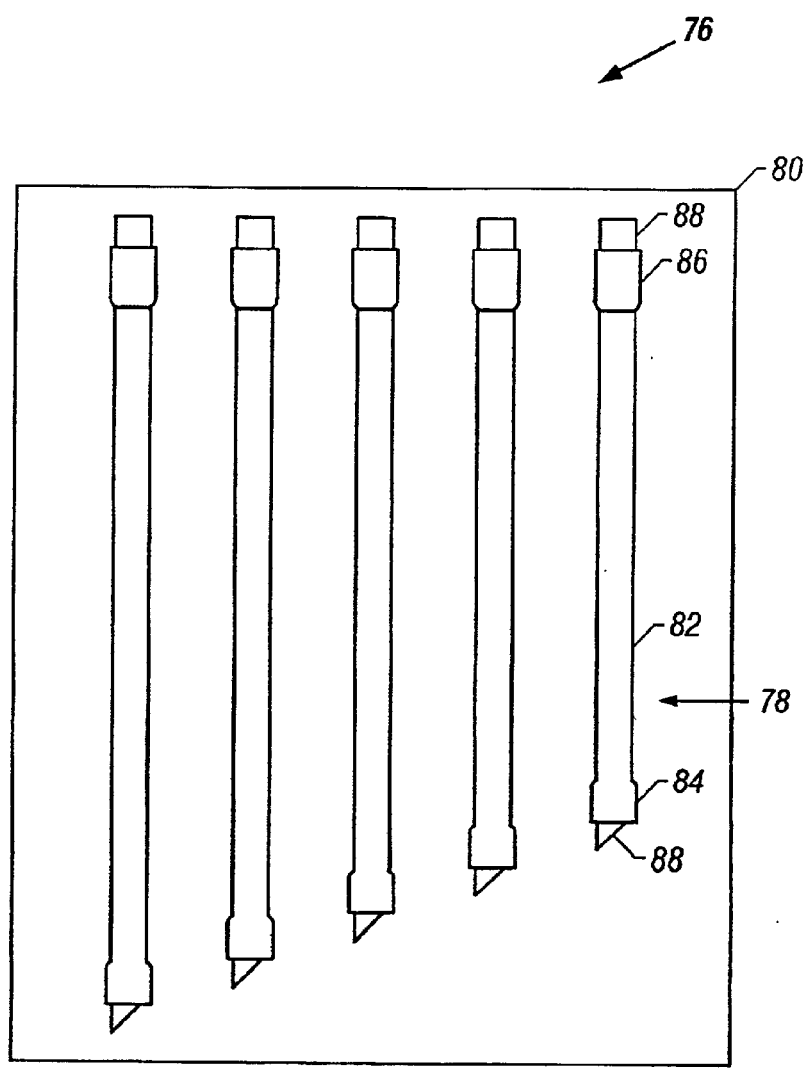
FIG. 6B shows a panel of measurement grafts useful to determine an appropriate length for the graft vessel to be prepared.

FIG. 6A shows a die (70) with grooves (72) that may be used to guide a scalpel or other cutting instruments to trim a graft (6) placed within partial bore (74) to achieve any of the graft configuration shown in FIGS. 6A–6C. In preparing the graft end configuration shown in FIG. 5B, a first cut is preferably made at a 45° angle to define the open heel (64). Then a 30° follow-up cut is made to define side portions (68). In preparing a graft as depicted in either of FIG. 5A or 5B, it may also be desired to create a rear slit. This is currently performed by taking the graft out of die (70) and manually cutting it with Potts scissors for a length up to about 4 mm to 10 mm. This allows for further advancement of graft (6) over fitting (10) to provide increased coverage.

A graft/connector combination with at least a distal connector (4) is preferably prepared before producing the arteriotomy into which this connector is preferably placed. In determining the appropriates size of connector (4) and length of graft, measurements are taken. The size of the connector depends on the size (particularly the diameter) of graft that is harvested or otherwise made available for use.

The length to which graft (6) should be cut may be determined by simply measuring the distance between anastomosis target sites. A preferred manner is, however, to take a measurement by reference to a group or panel (76) of measurement graft/connector members (78) such as shown in FIG. 6B. Like a panel of different optics that an optician may use to determine the proper match for a patient, comparison of different members (78) provided in panel (76) to the relevant anatomy provides a physician with the ability to quickly and easily visualize and estimate the ideal graft length. The length of each unit is advantageously identified by printing upon each measurement members (78) or in connection with an optional container (80). Either way, utilizing measurement members (78) provides a much more accurate gauge of the proper length of a host vessel since each more realistically spans the distance between target sites. Most preferably, each member (78) conforms to anatomy and approximates the angle(s) at one or both anastomosis sites.

To achieve such results, measurement members (78) preferably include a central section (82) adapted to model the compliance of a graft to be used. Each member also preferably includes an end (84) adapted to model the properties of a connector according to the present invention. The opposite end (86) of each member may be adapted to model a proximal anastomosis connector. A preferred manner of producing measurement members so-adapted or configured is with PTFE tubing ranging in diameter from about 2 mm to about 6 mm and a length between about 60 mm and about 150 mm together with actual connector members or pressed-in inserts (88). The inserts may be made of simple plastic pieces or otherwise.

Now that many of the device features of the invention have been described, the methodology associated therewith is set forth in the order in which it is preferred that a surgeon or surgical team take action to perform a coronary bypass procedure. Variation of this procedure is, of course, contemplated. Furthermore, it is to be understood that the devices described herein may be used outside of this context.

This being said, after opening a patient and taking a measurement between intended target sites for proximal and distal anastomoses or by reference to the panel of measurement members (78) discussed above, a graft member (6) of sufficient length is obtained. Typically this will be a saphenous vein. Alternately, another harvested vessel (such as the lima or radial artery), a synthetic vessel or a donor vessel may be used as a graft.

Especially in the case where an organic member is used, the vessel will be sized to determine the appropriate connector size. This is preferably done with reference to the inner diameter (90) of the graft by inserting pins of increasing size (e.g. by 0.25 increments) until the graft no longer easily fits over a given pin. The size of the largest pin over which graft easily fits over sets the inner diameter of the graft.

Next, a connector for producing an anastomosis at a desired angle, and having an appropriate size is chosen. The size of fitting (10) and optional collar (12) is preferably the first incremental size over the inner diameter of the graft. It is contemplated that connector component sizes may be sized to fit grafts of a diameter from about 2 mm to about 6 mm progressively, at 0.5 mm increments.

Once appropriately sized connector components are chosen, a graft is skeletonized 10 mm away from the end to be used in connection with the distal anastomosis. This may be accomplished by holding the adventitial tissue away from the graft with forceps and removing selected portions with Potts scissors. At this stage, graft (6) is cut in such a manner as discussed above and advanced over fitting (10) into a position as depicted in FIGS. 1, 2 or 12A.

Advancing graft (6) over fitting (10) may be accomplished while holding fitting (10) with a clamp tool (e.g., a hemostat) and using forceps on either side of graft (6) to pull it over the fitting. If a collar is included in connector assembly (4), it is advanced over graft (6) while holding graft end (48) to fitting front segment (16). Doing so with a clamp tool ensures the graft/fitting alignment is not changed. Once in place over a fitting (18), graft (6) may be trimmed to more closely conform to the shape of connector elements, particularly the exterior of any collar (12) used. Trimming a graft in this manner may be particularly appropriate in instances where the graft used is simply prepared by taking a vessel, cutting it at 90° relative to its length and then creating a rear slit along its length as described above.

Figure 9A:
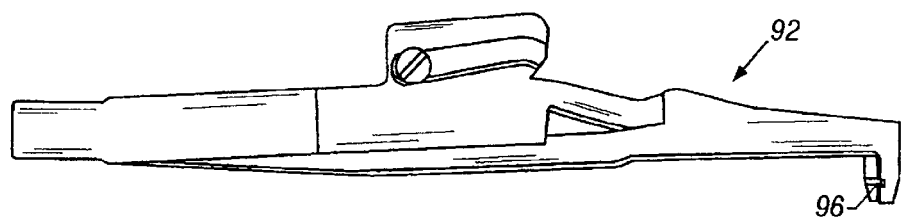
FIGS. 9A and 9B show side and top views of a spreader specifically adapted to open a collar.
Figure 9B:
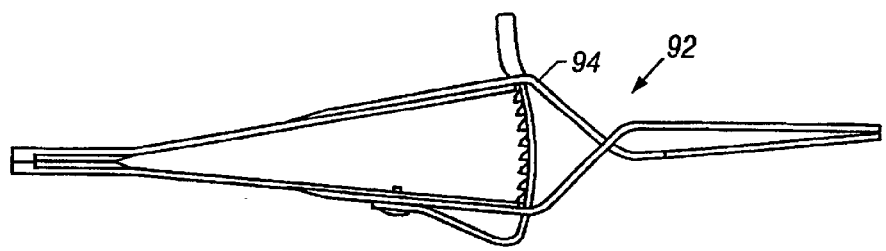
Figure 10:
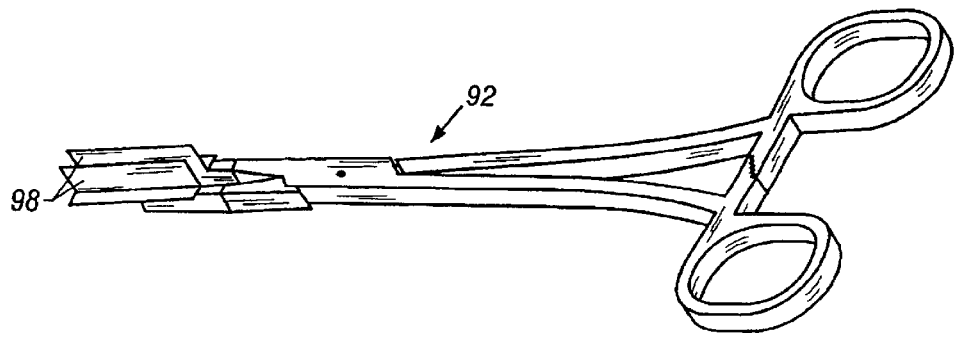
FIG. 10 shows an oblique view of another spreader adapted to open a collar.

A number of spreading mechanisms maybe used to hold collar (12) open to advance it over graft (8). FIGS. 7, 9A, 9B and 10 depict optional spreader devices (92). While spreader (92) in FIG. 7 has additional utility as described below, those depicted in FIGS. 9A and 9B and 10 are more specialized. The spreader in FIGS. 9A and 9B include an adjustable locking feature (94) as well as grooves (96) to capture the opposite sides or rib segments (46) of a collar. The spreader variation shown in FIG. 10, is a modified clamp. Bracketed ends (98) affixed to an otherwise common implement provide the means to open collar (12) to place it on graft (6) loaded onto fitting (10). Such an instrument may be more familiar to a surgeon, and therefore preferred.

In placing collar (12) over graft (6), it is to be set in relation to fitting (10) in a complementary manner. When optional tabs (22) and (24) are provided, these features can easily be used to help align a fitting and a collar relative to each other. Either way, once collar (12) and fitting (10) are properly aligned, collar (12) is released onto graft (6). Following this, any tabs and/or locking features (36) are engaged with each other and a final check is made to ensure accurate component placement and graft coverage.

In the event a proximal connector is to be used to complete a coronary bypass procedure, it may be connected to graft (6) in a similar fashion or as described variously in the references cited above. Still, as noted above, a distal connector may alone be used, with the proximal anastomosis to be accomplished otherwise. While it need not be the case, the distal connector will preferably be deployed before making the proximal connection.

Once a graft/connector combination is prepared, the assembly is then preferably engaged with a deployment device (52). The deployment device may be provided as in FIG. 12A, however, alternate devices are envisioned.

Figure 11A:
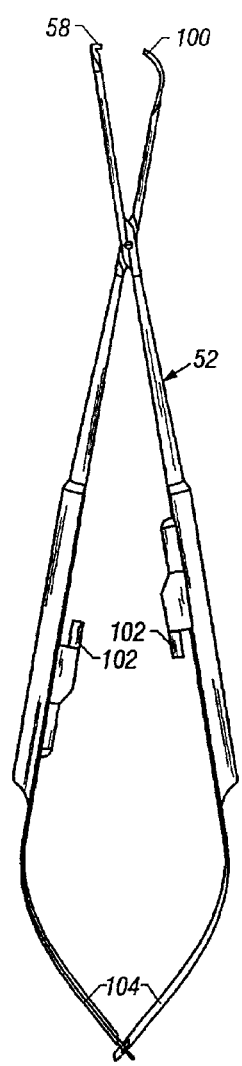
FIG. 11A show a side view of an instrument with a head adapted to deploy a connector.
Figure 11B:
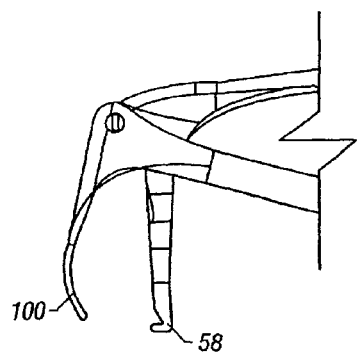
FIG. 11B shows an alternate head configuration for the instrument in FIG. 11A, this head configuration adapted for deploying a connector while holding the instrument at a different angle.

FIG. 11A shows a deployment device (52) similarly adapted to draw back band (40) while advancing rear segment (18) in a manner similar to the deployment device shown in FIG. 12A. Interface section (58) captures band (40) while hook (100) advances rear segment (18). To accommodate differences in anatomical access locations or paths, it is also possible to orient the end of the deployment device shown in FIG. 11A at another angular orientation as shown in FIG. 11B. In this case, the instrument head is shown rotated approximately 90°. It is also noted that the deployment device in FIG. 11A optionally includes interlocking members (102) and sprung arms (104), that work in conjunction with each other to provide a more user-friendly device able to provide a more stable, user-friendly device to maintain a connector in a state ready for deployment.

Figure 13A:
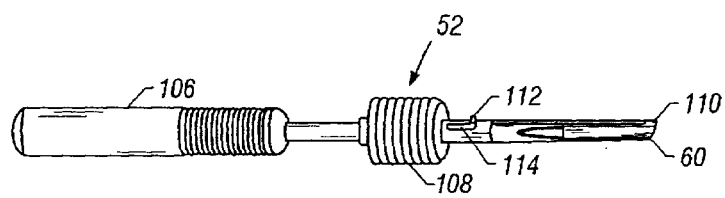
FIGS. 13A and 13B show side views of another instrument for deploying a connector, the instrument positioned in retracted and extended states, respectively.
Figure 13B:
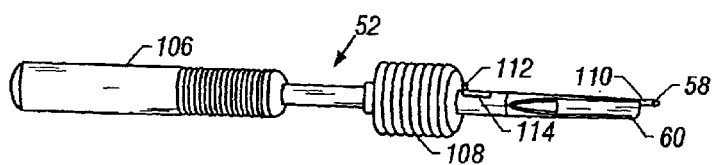

Alternate deployment mechanisms are portrayed in FIGS. 13A, 13B, 14 and 15. The deployment device in FIGS. 13A and 13B includes a primary handle (106) and an actuator handle (108). When actuator handle (108) is advanced, band grasping interface member (110) with interface section (58) is advanced as shown in FIG. 13B. Pin (112) within opening (114) limits the extent to which it may be advanced or withdrawn. When band interface member (110) is retracted as shown in FIG. 13A, to draw band (40) back from lead segment (16), the rear segment of a fitting abuts interface section (60) to ready the connector for deployment.

Figure 14:
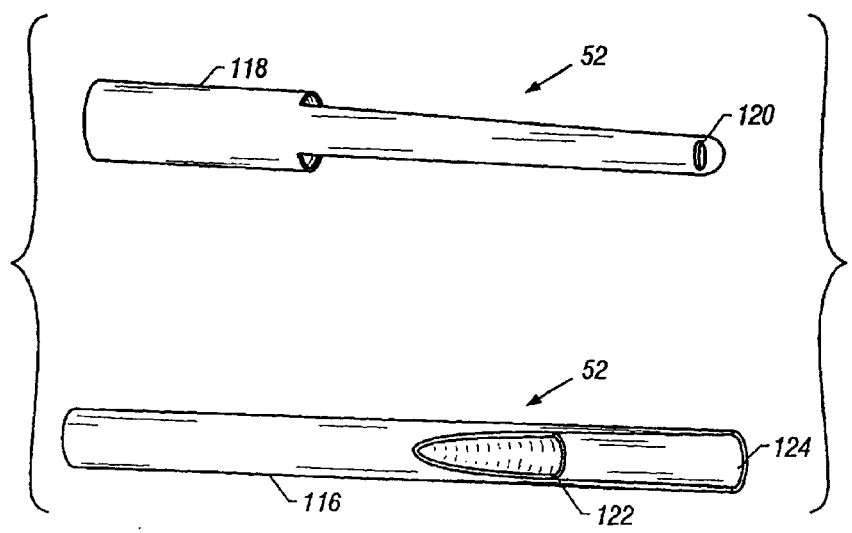
FIG. 14 shows a side view of components to form another instrument for deploying a connector.

FIG. 14 shows another type of deployment device (52). In this variation, a handle portion (116) and an actuator portion (118) to be slidably received by handle portion (116) is used by hooking rear segment (18) in retractor opening (120) and drawing it into recess (122) when connector (4) is set in receptacle section (124).

Figure 15:
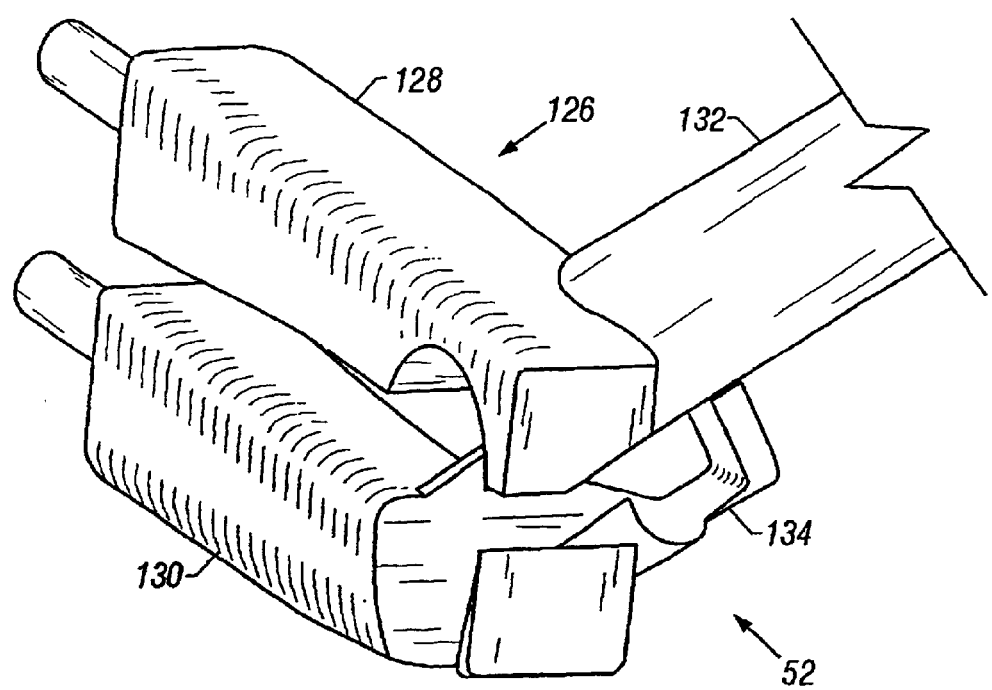
FIG. 15 shows an oblique view of a end portion for another instrument for deploying a connector.

FIG. 15 shows an end section (126) of yet another type of deployment device. This variation is adapted for sideways deployment of a connector. In combination with each other, top and bottom portions (128) and (130) restrain a connector, compressing rear section (18) ready for connector deployment. A deployment mechanism incorporating side-deployment end section (126) may be advantageously used in situations where access to the host vessel is hindered by little clearance due to a small thoracic cavity or difficult vessel orientation. The graft of a graft/connector combination is received in guide section (132), and stop (134) limits how deeply the combination may be set into the deployment device end section (126).

Figure 11C:
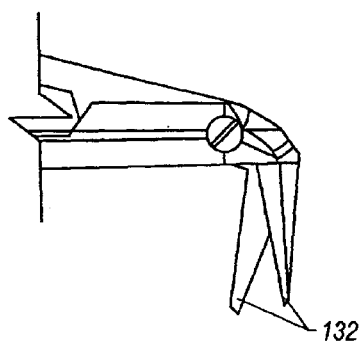
FIG. 11C shows an scissors-type head configuration that may be used with the handle portion of the instrument in FIG. 11A.

It is preferred that connector (4) be set and prepared for deployment within a deployment device before taking invasive action at the target site for a distal anastomosis. Regardless, a distal anastomosis site is prepared by creating an initial puncture, for instance, with the tip of a number 11 blade scalpel. Next, this opening is preferably extended longitudinally with scissors to about 3 mm to 7 mm in length depending on the vessel size. Most often, a longitudinal slit of about 5 mm is preferred. Scissors are advantageously provided in connection with an instrument as shown in FIG. 11A, modified with scissors ends (132) as shown in FIG. 11C. Otherwise, standard Potts scissors may be used.

Figure 7:
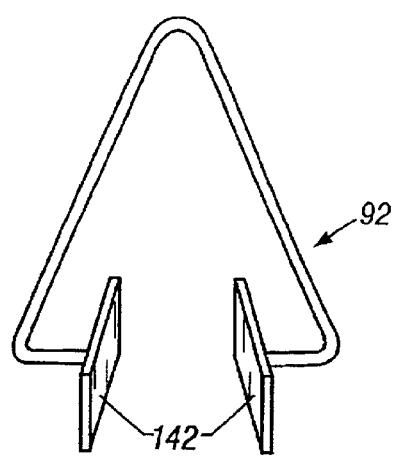
FIG. 7 shows an oblique view of a spreader.
Figure 8:
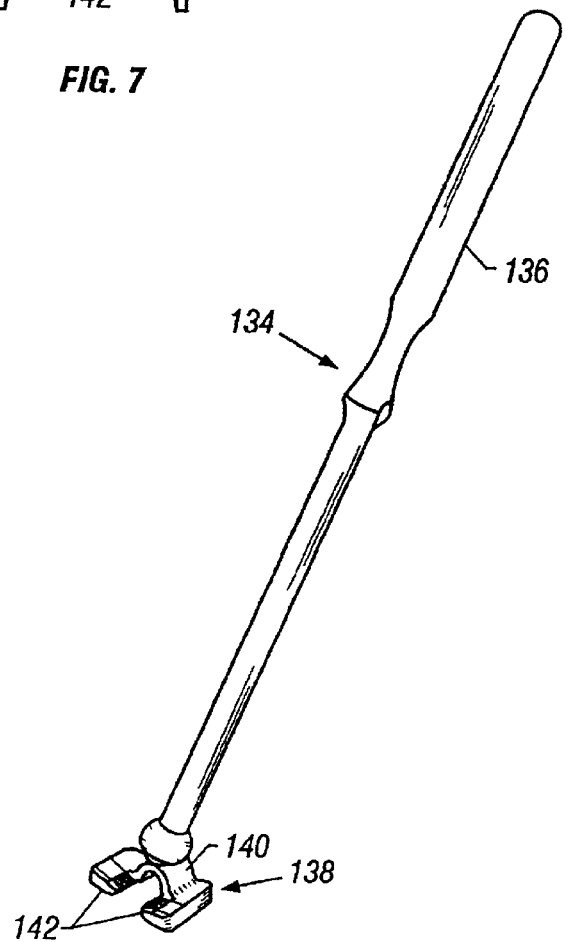
FIG. 8 shows an oblique view of a stabilizer.

It may be preferred to use a stabilizing member (134) to help accomplish the arteriotomy. FIG. 8 shows a suitable device. It includes a handle (136) and an endpiece (138). A bridge (140) provides clearance for a coronary artery, while feet (142) are set against the heart of a patient. Gradations or other indicators in endpiece (138) help provide a visual indication for creating appropriately long arteriotomy. Once an arteriotomy of sufficient length has been created, it is preferably held open by arms (142) of a spreader (92) as shown in FIG. 7.

At this stage, connector (4) is deployed. This is preferably performed by advancing leading section (16) through the arteriotomoy, and then such lateral features (20) of fitting (10) as may be provided. Deflected rear segment (18) is then advanced into host vessel (8) and released to assume a position as shown in FIG. 1 in order to secure the connector.

Particularly in those variations of the invention as described above where movement of rear segment articulates side portions (20), movement of rear segment (18) to an host-vessel engaging position will also cause affected side portions (20) to engage the sides of host vessel (8) to maintain connector (4) in place.

In instances when a collar (12) is used in connector (4), it is also released to compress front portion (48) of graft (6) against host vessel (8). Release of collar (12) may also result in compressing graft (6) against portions of host vessel (8) opposed by lateral fitting portions (20), especially if complimentary lateral collar portions (44) are provided.

Once in place, the completed anastomosis is checked for leakage. This may be done before and/or after an anastomosis at the proximal site is complete. At minimum, an inspection of the distal connection should be made when blood is flowing through graft (6). If leakage is detected, and it cannot be remedied by adjustment of the graft or collar, the anastomosis site may be packed or bioglue (e.g., as available through Cryolife in Kennesaw, Ga.) or a stitch of suture material may be applied.

In extremely rare instances where these steps do not prove adequate, it may be necessary to remove connector (4). After removing with any supplemental means applied in effort to provide hemostasis, connector (4) may be removed by reversing the procedure for its deployment.

Now, returning to the elements of connector (4), optional inventive features and a manner of manufacture is described. A preferred manner of producing connector components according to the present invention is by machining tubing to include features that may be bent and set into shape to produce connector elements like those depicted in FIGS. 1, 2, 3A, 3B, 4A, 4B and 12A. Shapes so produced may be referred to as wireforms.

The machining may be accomplished by electron discharge machining (EDM), mechanically cutting, laser cutting or drilling, water-jet cutting or chemically etching. It is to be noted that portions of the connectors may be fabricated as a separate components and bonded by spot welding, laser welding or other suitable manufacturing process to form complete structures. Typically, after whatever cutting or forming procedure is employed, the material is set in a desired final shape. Where a metal is used, one or more flexure steps followed by heating will accomplish this. If the connector elements are made of alternate material such as a plastic or a composite, other forming procedures as would be apparent to one with skill in the art may be used.

Preferably, connector elements are made from a metal (e.g., titanium) or metal alloy (e.g., stainless steel or nickel titanium). Other materials such as thermoplastic (e.g., PTFE), thermoset plastic (e.g., polyethylene terephthalate, or polyester), silicone or combination of the aforementioned materials into a composite structure may alternatively be used. Also, connectors fabricated from nickel titanium may be clad with expanded PTFE, polyester, PET, or other material that may have a woven or porous surface. The fittings may be coated with materials such as paralyne or other hydrophilic substrates that are biologically inert and reduce the surface friction. To further reduce the surface tension, metallic or metallic alloy fittings may be electropolished. Evidence suggests that electropolishing reduces platelet adhesion because of the smooth surface. Alternatively, the fittings may be coated with heparin, thromboresistance substances (e.g., glycoprotein IIb/IIIa inhibitors), antiproliferative substances (e.g., rapamycin), or other coatings designed to prevent thrombosis, hyperplasia, or platelet congregation around the attachment point between the bypass graft and the host vessel. Alternatively, a material such as platinum, gold, tantalum, tin, tin-indium, zirconium, zirconium alloy, zirconium oxide, zirconium nitrate, phosphatidyl-choline, or other material, may be deposited onto the fitting surface using electroplating, sputtering vacuum evaporation, ion assisted beam deposition, vapor deposition, silver doping, boronation techniques, a salt bath, or other coating process.

A still further improvement of the fittings is to include beta or gamma radiation sources on the end-side fittings. A beta or gamma source isotope having an average half-life of approximately 15 days such as Phosphorous 32 or Paladium 103 may be placed on the base and/or petals of the end-side fitting using an ion-implantation process, chemical adhesion process, or other suitable method. Further details as to optional treatments of connectors according to the present invention are described in 10.00. Of course, connector fitting (10) and any associated collar (12) may be made differently. To avoid electrolytic corrosion, however, dissimilar metals should not be used.

Preferably, NiTi (Nitinol) tubing or flat stock is used to produce connector components. Irrespective of material format, a preferred alloy includes a 54.5–57% Ni content, and a remainder Ti by weight (less minor amounts of C, O, Al, Co, Cu, Fe, Mn, No, Nb, Si and W) is used. Such alloy has an $A_f$ for at about −10 to −15° C. Consequently, for typical handling and in use, the material will exhibit superelastic properties as is most desired.

Still, it is contemplated that connectors according to the present invention may utilize thermoelastic or shape memory characteristics instead, wherein the material of either or both fitting (10) and connector (12) change from a martinsitic state to an austenitic state upon introduction to an anastomosis site and exposure to a sufficiently warm environment. Taking advantage of the martinsitic state of such an alloy will ease deflecting rear segment (18) and lead band (40) and maintaining their positions until placement.

Utilizing either thermoelastic or superelastic properties makes for a connector that can have certain members stressed to a high degree and return without permanent deformation from a desired position. However, it is contemplated that either or both fitting (10) and collar (12) may be made of more typical materials such as stainless steel or plastic. For fitting (10), this is feasible in view of the manner in which rear segment (18) is displaced for insertion into a host vessel. Hinge section (28) permits designs in which the stress applied by torsion is lower that applied in simply deflecting a rear petal or segment as shown and described in U.S. and foreign patents and applications entitled, "Improved Anastomosis Systems", U.S. patent application Ser. No. 09/730,366; "End-Side Anastomosis Systems", PCT Publication No. WO 01/41653; "Advanced Anastomosis Systems (II)" U.S. patent application Ser. No. 09/770,560.

This being said, FIGS. 16A–16C show views of a connector fitting (10) at an intermediate stage of production being made from tubing. The tube stock used to prepare distal connector fitting preferably has an outer diameter between 0.080 and 0.240 in (2 to 6 mm) and a wall thickness between 0.004 and 0.008 in (0.1 to 0.2 mm). Slightly larger diameter stock (or end product) will be used for each matching collar. The stock thickness for NiTi material used to form collars will typically have a wall thickness between about 0.04 in and about 0.08 in. Especially, for fitting (10) where it is possible to use thin stock in view of strength requirements, this will be preferred in order to minimally obstruct blood flow past the fitting. Larger connector components will typically be made of thick stock to account for increased stiffness required of such configurations relative to smaller ones.

In the piece shown in FIGS. 16A–16C, all the various elements described above in connection with completed fittings may be observed. However, only rear segment (18) is show set in its final, formed position. As with the other elements, rear segment (18) is cut in the tubing and initially appears aligned with the other features. Then, a technician deflects the segment from its initial placement in accordance with the arrow associated with segment (18). To set each element in its pre-operative location, the material is stressed and held at the desired position while heated or thermally formed to set its shape. The degree of bend in rear segment show is so extreme as to require sequential deflectation and thermal forming steps. As for the other elements to be set in a deflected shape as indicated by arrows associated therewith, a single deflection/thermal-forming cycle is adequate.

Figure 17A:
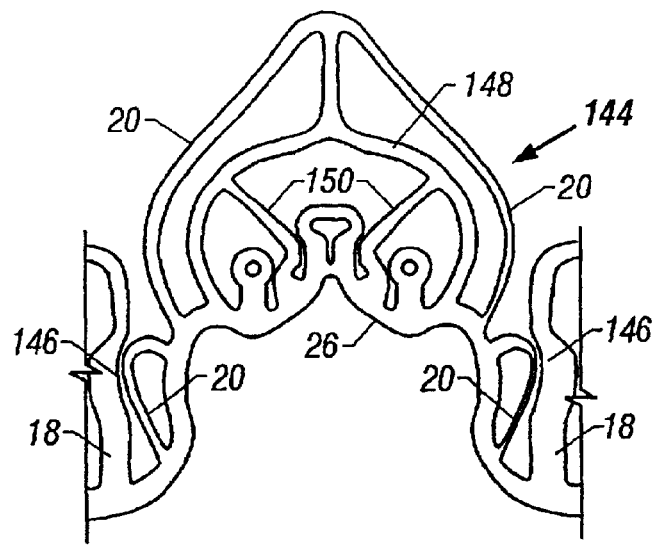
FIGS. 17A and 17B, 18A and 18B, and 19–22 show projected views of optional fitting features.
Figure 17B:
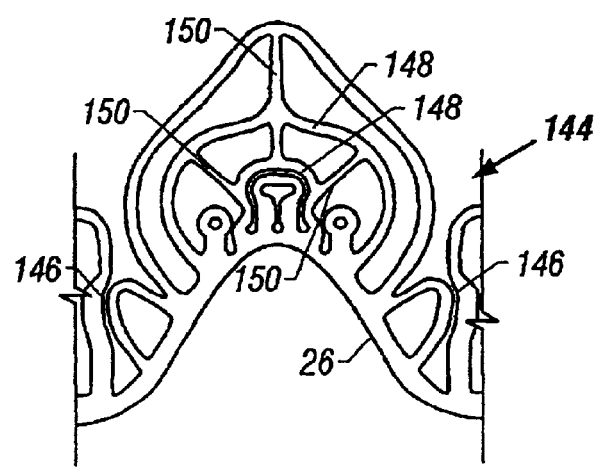

FIGS. 17A and 17B show splayed out views of a fitting according to the present invention. In interpreting these figures and those similar to them for the collars, it need only be appreciated that each flattened form represents a pattern (144) for cutting tube or flat stock to be shaped into a fitting or connector. When fitting pattern (144) is cut in tubing, it completely wraps around the tube forming a seamless piece very similar to that in FIGS. 16A–16C. When flat stock is used, another forming step is used to produce a round or ovalized body with which to work with. The ends of the body may then be joined. Alternately, any gap or split may be left open to provide a measure of especially compressibility in the fitting. What is more, it is contemplated that a gap or split may be formed in a fitting made from tube stock to provide such compliance to connector.

One way in which a fitting according to pattern (144) in FIG. 17A differs from that in FIGS. 16A–16C, however, is by relieved sections (146) in rear segment (18). This allows for relatively larger rear lateral portions (20). Fitting pattern (144) in FIG. 17B includes similar features. It is further distinguished, however, by its smaller size suited for cutting into a smaller diameter tube (or in flat stock) to form a smaller connector (3.0 mm diameter in comparison to 3.5 mm diameter). Due to the smaller size, of the fitting, a substantially regular opening (26) is provided. In contrast, the variation in FIG. 17A includes a nonlinear or irregular opening shape, similar to that shown in FIGS. 16A–16C. This has been found to advantageously reduce the a wound-healing/hyperplastic response at the site. Each of the fitting patterns (144) in FIGS. 17A and 17B include various bands (148) and runners that provide a sort of latticework or wireform to give substance to the connector while minimizing material usage.

Figure 18A:
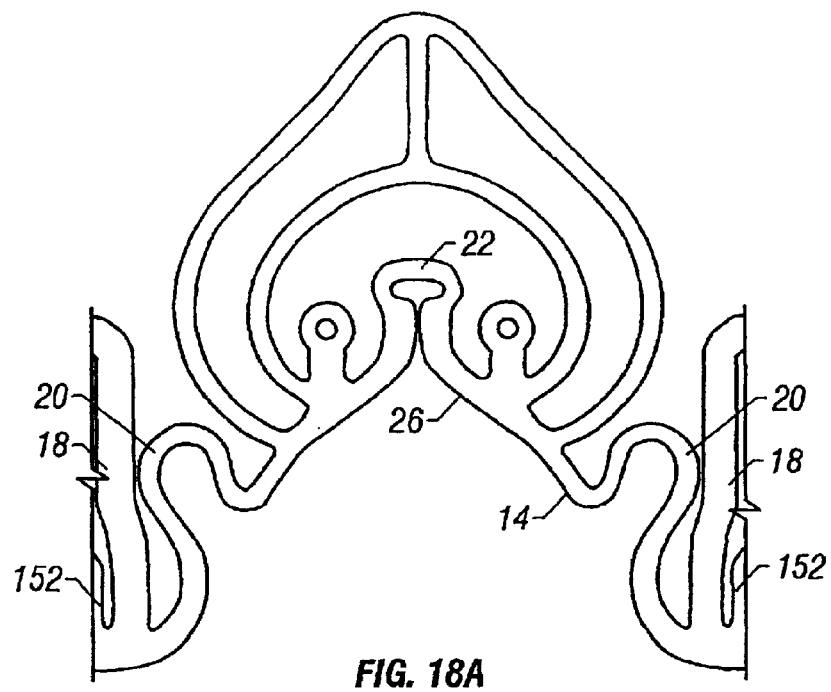
Figure 18B:
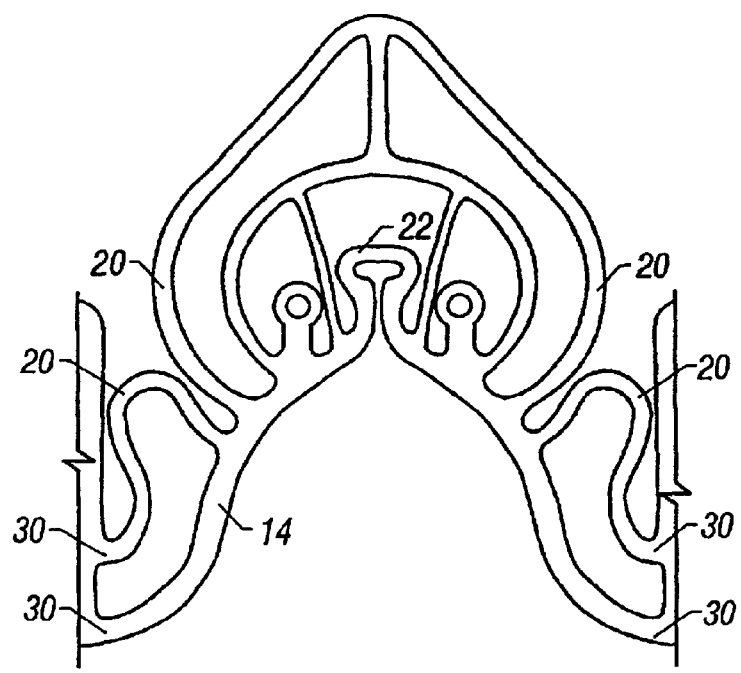

FIGS. 18A and 18B show patterns for connectors that are similarly constructed. In these, opening (26) becomes less regular as breaks in the base or body (14) of the fitting are observed. In a fitting made in accordance with FIG. 18A, those breaks occur in connection with rear lateral portions (20) and at lead tab (22). The fitting pattern in FIG. 18A also provides a tang (152) to grab the heel of a graft to assist in graft loading and/or placement. The switchback providing each of the lateral portions (20) not only assists in providing a non-circular or irregular shape to assist with issues of hyperplastic response, but also provides a measure of axial flexibility to a fitting including such a feature. The break in the base of the fitting at lead tab (22) provides a measure of radial compressibility to the fitting.

In the fitting variation shown in FIG. 18B, a break at tab (22) is also provided. However, base (14) provides more complete support to elements around the fitting. The manner in which rear lateral portions (20) are attached to rear segment (18) is also worthy of note. As discussed variously above, such a configuration allows for actuation of lateral portions connected to the rear segment. Also, it provides a pair of torsional members (30) on each side of rear segment (18) around which to hinge.

Figure 19:
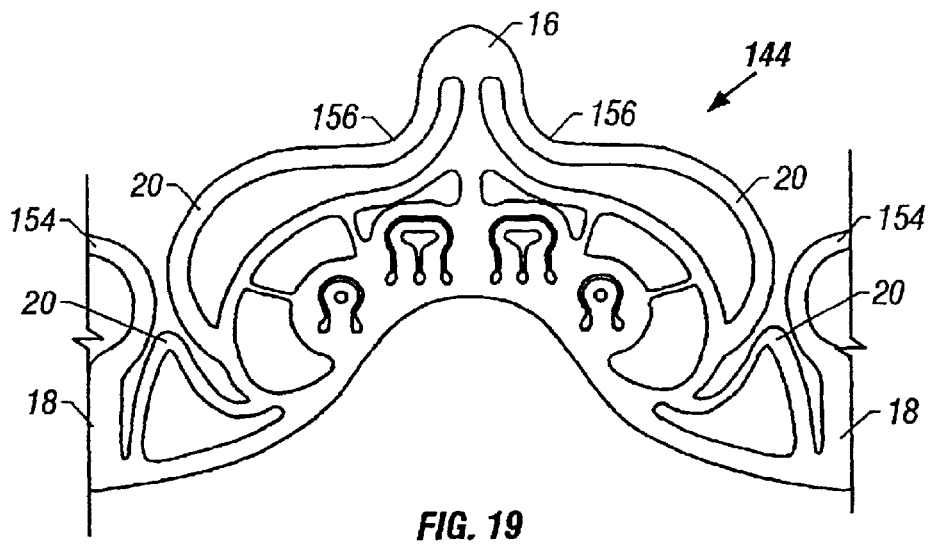
Figure 20:
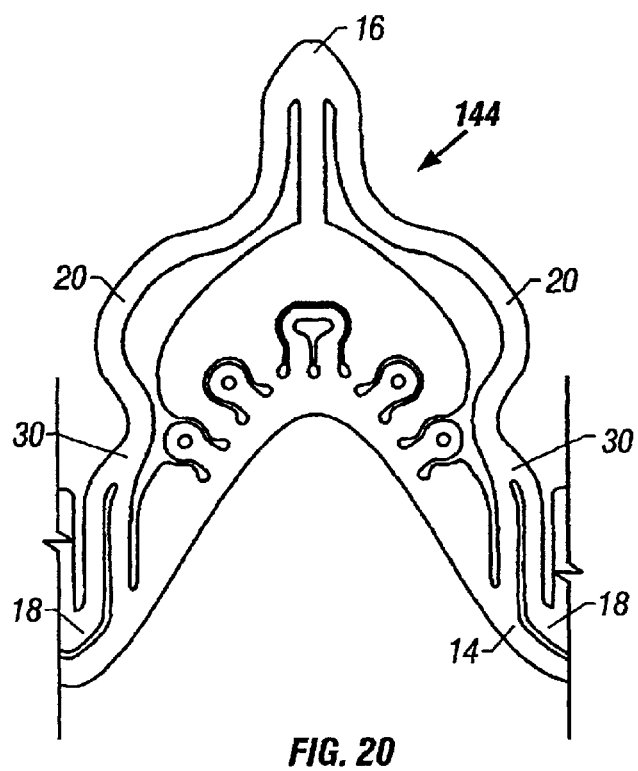

FIGS. 19 and 20 show fitting patterns (144) with additional inventive features. A connector to be formed according to the pattern in FIG. 19 will have a rear segment (18) that includes an enlarged end (154). The increased coverage of end (154) may provide a more secure connection or a relatively less traumatic interface with host vessel (8). However, unless finely tuned in size, enlarged end (154) can present clearance challenges in deployment. Likewise, a tight transition (156) from lead section (16) to forward side sections (20) may provide some impediment to introduction through an arteriotomy. A more preferred approach is shown in connection with FIG. 1 where a more gradual transition is made between lead segment (16) and side portions (20). Still, such a profile may be difficult to achieve in relatively large diameter connectors (i.e., on the order of 6 mm in diameter) such as shown in FIG. 19.

Regardless, it is noted that fittings as shown in FIGS. 1, 19 and 20 share a common feature in a relatively discrete front segment (16) as compared to other fittings shown herein. This may assist in connector penetration and dilation of an arteriotomy during insertion. A broader front section (16) as shown in FIGS. 17A–18B may, however, be more advantageous from the perspective of the hemostasis due to greater coverage area.

A fitting according to the pattern shown in FIG. 20 includes further distinguishing characteristics. Here rear segment (18) originates in a different manner than shown in connection with the other fittings. In this instance, torsion sections (30) are not provided in connection with base (14) near opening (26) but are positioned adjacent lateral portions (20). Provided in this manner, no medial bend (32) or less bend in segment (18) is required to place rear segment end (154) in position to fulfill its task. In a fitting formed with a rear segment (18) oriented according to the approach in FIG. 20, segment (18) may be flexed outward from the connector body and set in shape by thermal forming by a single cycle. To use the fitting, rear segment (18) is flexed backward rather than forward. Formation of the fitting in this manner provides advantages in that less stress is applied to rear segment (18) in thermal forming it as shown in connection with the other figures. This makes for a stronger fitting, with rear segment less prone to failure due to high stresses during deflection for deployment or fatigue.

Figure 21:
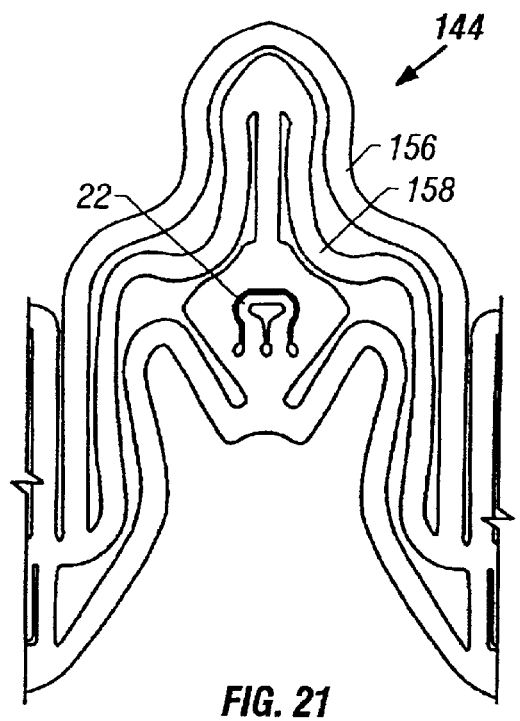

The pattern in FIG. 21 provides for a fitting in which a graft can be sandwiched between outer band (156) and inner band (158). In this manner, the outer band acts like collar band (40) to hold graft (6) against host vessel (8). Tab (22) is provided to help grip graft (6) as shown and described in connection with FIG. 1.

Figure 22:
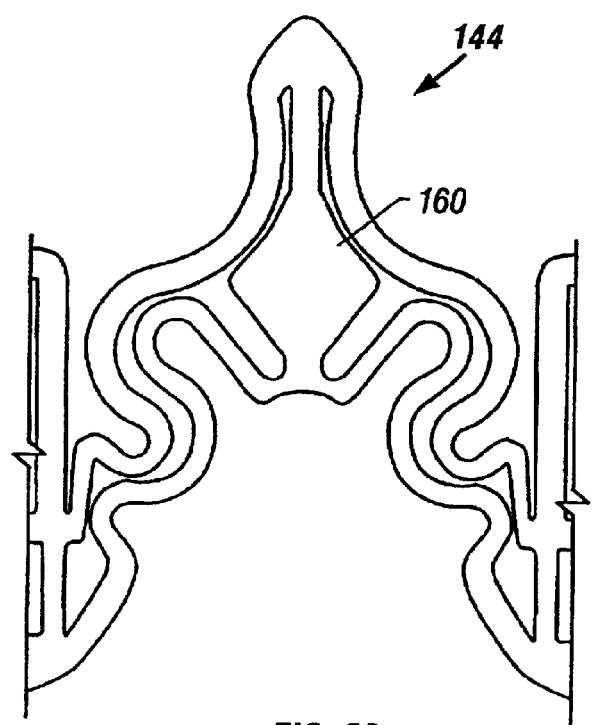

The pattern in FIG. 22 provides for a fitting with multiple undulations adapted to provided a measure of both axial and radial flexibility. Flexible fittings work particularly well with a collar. Especially in connection with a collar having locking members, it is useful to be able to compress the fitting when locking the collar around it so that upon expansion of the collar around the fitting to its locked limit, a graft is snugly captured between the fitting and the collar.

However, another feature of fitting pattern (144) shown in FIG. 22, makes a fitting so configured well suited for use without a collar. The absence of a tab at medial portion (160) provides a surface upon which to apply a bioadhesive to directly attach graft (6) to the fitting.

FIGS. 23–27B show patterns (162) for creating collars (12). Collars may be made in a similar fashion to the fittings as described above. Collars geometry is advantageously set to correspond in angle to the fitting chosen to form a matched set.

Figure 23A:
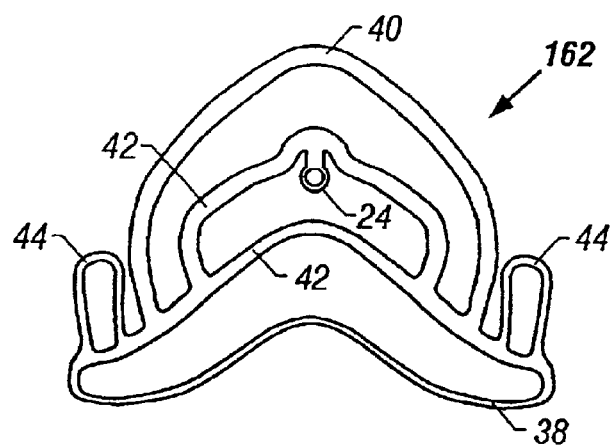
FIGS. 23A and 23B, 24A and 24B, 25, 26A–26C and 27A and 27B show projected views of optional collar features.
Figure 23B:
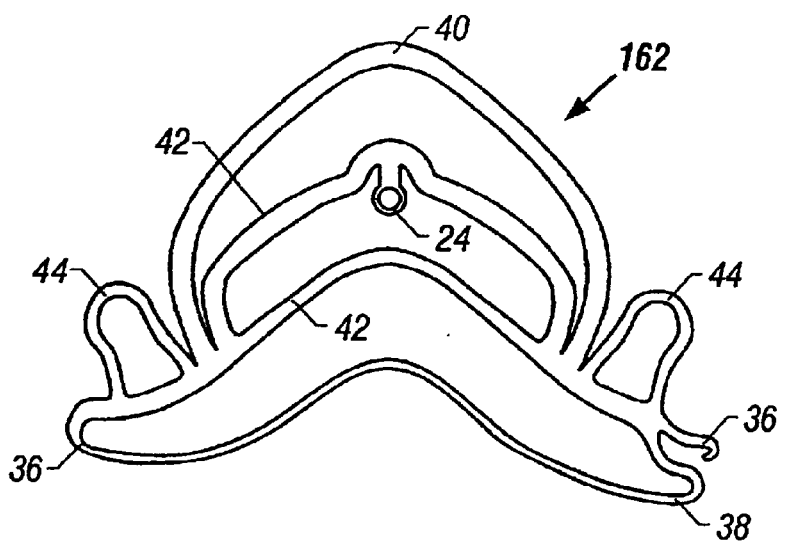

FIGS. 23A and 23B show projections to produce collars substantially as described above. A notable distinction between the two is the inclusion of locking features (36) in the later image.

Figure 24A:
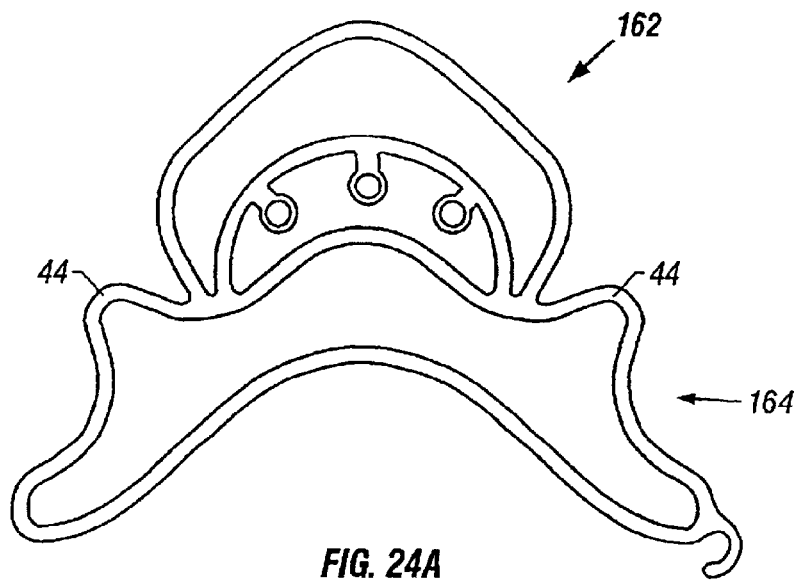
Figure 24B:
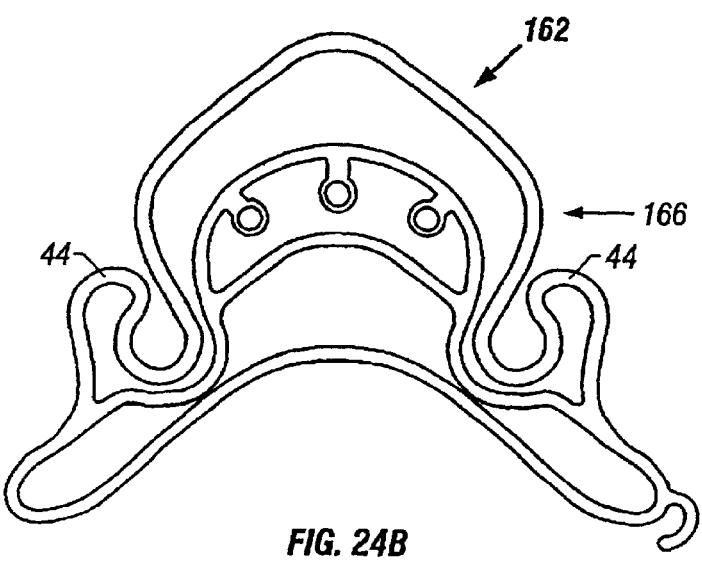

FIGS. 24A and 24B depict similar collars, except that additional tabs (24) are included in each. Also the manner of providing lateral portions (44) differs. The are no longer discreet members as shown in FIGS. 23A and 23B. Instead, in the variation shown in FIG. 24A, they are provided in connection with an proximal section (164) of the collar. In the variation in FIG. 24B, they are provided in connection with a distal section (166) of the collar. An advantage of the approach in FIG. 24A is that a stiffer forward section results providing greater force bearing upon graft (6) for improved hemostasis. An advantage of the approach in FIG. 24B is that upward deflection of distal band (40) causes, lateral portions (44) flex outward to provide additional clearance for connector insertion.

Figure 25:
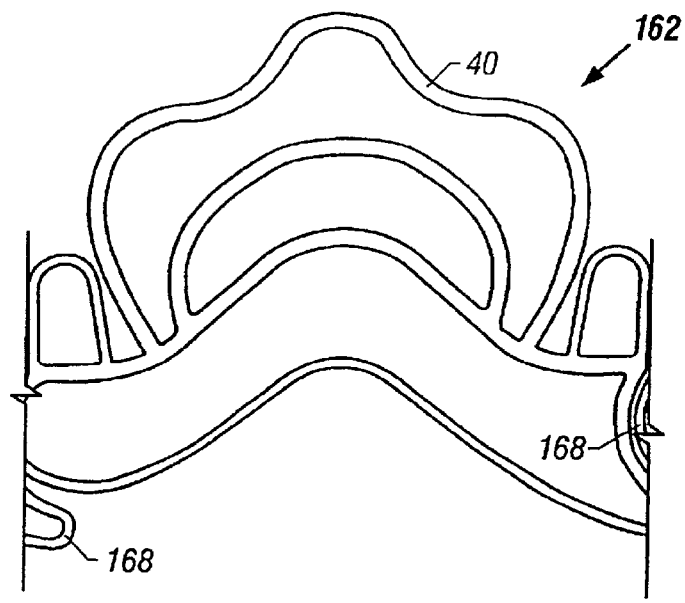

FIG. 25 shows a projection (162) configured to provide a collar (12) with overlapping ends (168). This avoids the production of a significant seam at the rear of a graft, thereby providing more support and improving graft patency. Another optional feature shown in connection with FIG. 25 (see also FIG. 27B) is a distal band shape intended be a mirror or complement the front portion of a matching fitting.

Figure 26A:
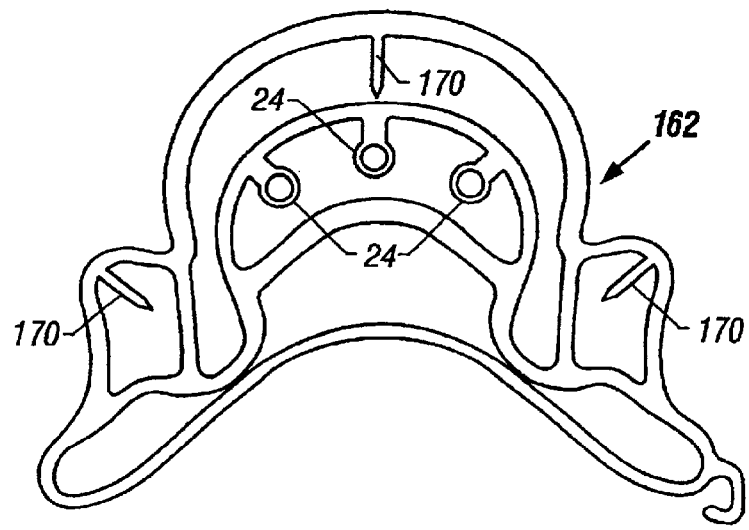
Figure 26B:
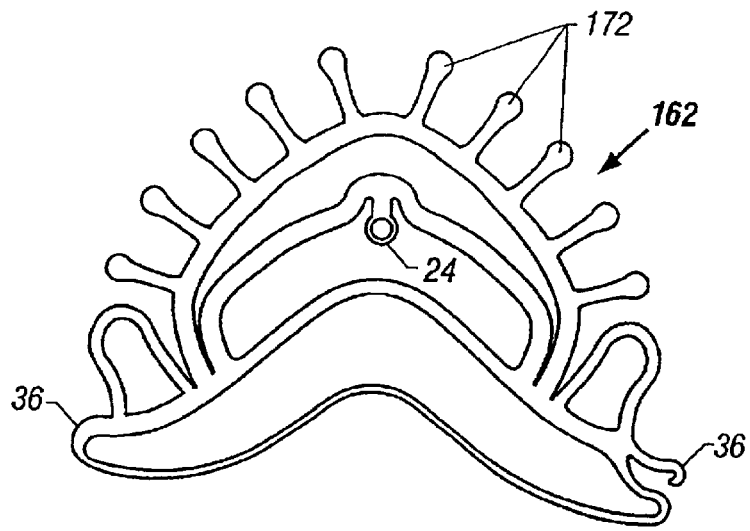
Figure 26C:
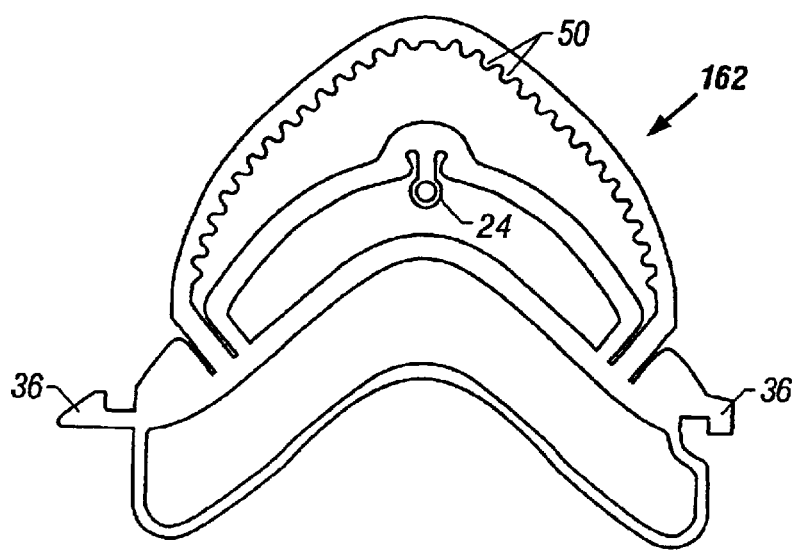

FIGS. 26A–26C show collar projections (162) including various retention features for grasping a graft (6) in addition to any tabs (24) provided. The variation in FIG. 26A includes barbs or tangs (170). The variation in FIG. 26B includes elongate tabs or fingers (172). The variation in FIG. 26C includes undulations (50) as described above. The variation in FIG. 26C also includes a different type of locking mechanism (36) than observed elsewhere in the figures. A lead-in feature is provided so a simple squeezing application of force the sides of the collar locks it.

Figure 27A:
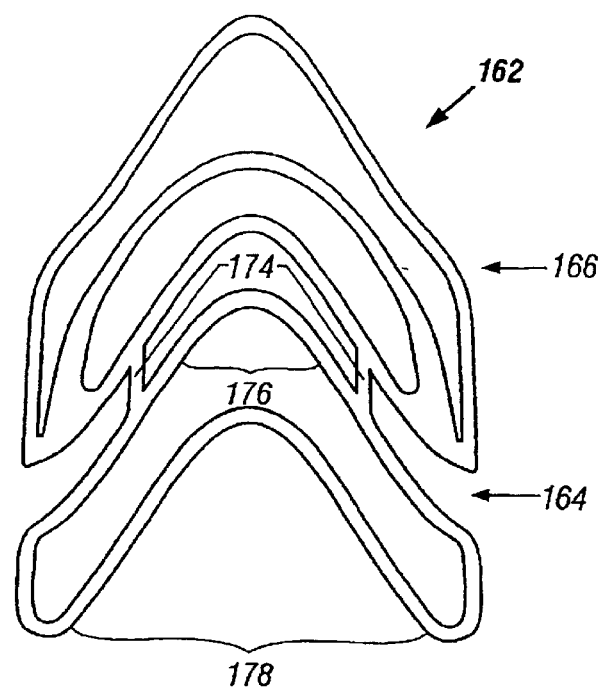
Figure 27B:
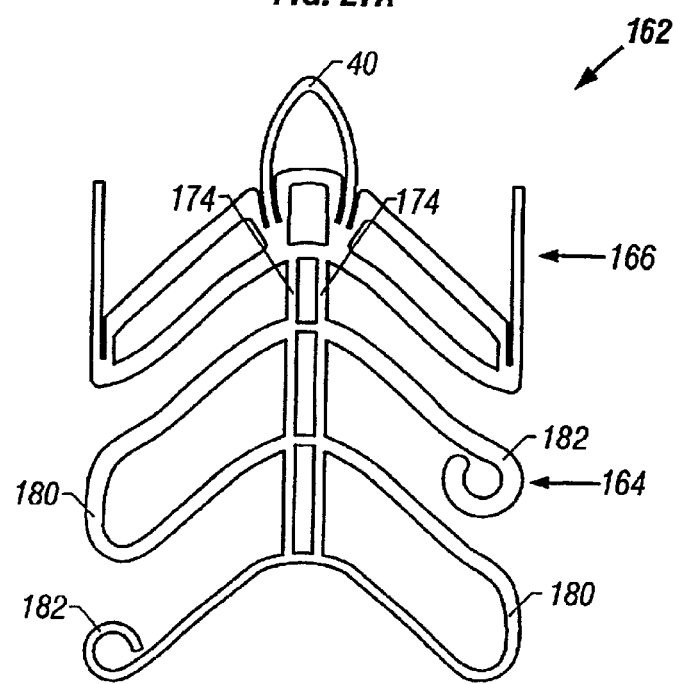

FIGS. 27A and 27B show examples of other features that may be included in collars according to the present invention. Fittings in accordance with each of these projections utilize distal section (166) to secure a graft about a fitting. The proximal section (164) in each serves to relieve strain on the graft. By avoiding the use of a pair or rib segments (46) along the length of the collar as shown in connection with the collar in FIG. 12A and instead attaching proximal section features by bridge elements (174), greater flexibility is achieved for the portion of each fitting supporting the back of a graft. In the variation shown in FIG. 27A, the placement of the elements also results in different stiffness of band sections (176) and (178). In the variation in FIG. 27B, change in stiffness form one band section to the next is evident in view of the decreasing size of the material forming the same and the offset loop (180) and curl (182) features provided. Alternately, successive loops or curls may be employed. Any of these features alone, or in combination may comprise a means for strain relief on a graft. Still further optional features for collars used in the present invention may include any of those described in the references cited above.

The invention has been described and specific examples or variations of the invention have been portrayed. The use of those specific examples is not intended to limit the invention in any way. In all, it is to be understood that each of the features described in connection with the various connector components and projections for forming the same may be mixed and matched to form any number of desirable combinations. Further, it is contemplated that additional details as to the use or other aspects of the system described herein may be drawn from Abstract, Field of the Invention, Background of the Invention, Summary of the Invention, Brief Description of the Drawings, the Drawings themselves and Detailed Description and other background that is intended to form part of the present invention, including any of the patent applications cited above, each of which being incorporated by reference herein in its entirety for any purpose. Also, to the extent that there are variations of the invention which are within the spirit of the disclosure and are equivalent to features found in the claims, it is the intent that the claims cover those variations as well. All equivalents are considered to be within the scope of the claimed invention, even those which may not have been set forth herein merely for the sake of relative brevity. Finally, it is contemplated that any single feature or any combination of optional features of the inventive variations described herein may be specifically excluded from the invention claimed and be so-described as a negative limitation.

I claim:

1. An anastomosis connector system comprising a fitting comprising:
    a base adapted for attachment to a graft,
    a leading segment extending from said base and adapted for introduction into a host vessel;
    a rear segment extending from said base, wherein said fitting has a length dimension extending from said leading segment to said rear segment and has a width dimension transverse to said length dimension, wherein said length dimension is greater than said width dimension; and
    a hinge zone associated with said base and comprising at least one torsion member,
    wherein by means of said at least one torsion member said rear segment is torsionally deflectable about said binge zone relative to said base such that said fitting can be advanced into a host vessel and wherein, upon returning to a substantially undeflected position, said rear segment prohibits retraction of said fitting from the host vessel;
    wherein said fitting comprises a plurality of interconnected links having spaces therebetween and adapted to engage the inner surface of the host vessel wherein the area of contact between the interconnected links and the inner surface area of the host vessel is no greater than about 35% of the total area of the fitting upon forming an anastomosis.

2. The system of claim 1 wherein at least said leading and rear segments are formed from said interconnected links.

3. The system of claim 2 wherein said fitting further comprises at least one lateral portion positioned between said leading segment and said rear segment, and said at least one lateral portion is formed from said interconnected links.

4. The system of claim 3 wherein said at least one lateral portion provides a smooth transition between said leading segment and said rear segment.

5. The system of claim 1 wherein said base and said rear segment are positioned relative to each other wherein said graft is positioned at an angle with said host vessel upon operative engagement of said fitting within said graft and said host vessel.

6. The system of claim 5 wherein said angle is in the range from about 20° to about 70°.

7. The system of claim 1 wherein said leading segment has a rounded-toe configuration.

8. The system of claim 1 wherein said rear segment has an outwardly facing surface and an inwardly facing surface and further wherein at least a portion of said at least one torsion member faces said inwardly facing surface.

9. An anastomosis connector system comprising a fitting comprising:
- a base adapted for attachment to a graft,
- a leading segment extending from said base and adapted for introduction into a host vessel;
- a rear segment extending from said base, wherein said fitting has a length dimension extending from said leading segment to said rear segment and has a width dimension transverse to said length dimension, wherein said fitting has a tubular configuration along said length dimension; and
- a hinge zone associated with said base and comprising at least one torsion member,
- wherein by means of said at least one torsion member said rear segment is torsionally deflectable about said hinge zone relative to said base such that said fitting can be advanced into a host vessel and wherein, upon returning to a substantially undeflected position, said rear segment prohibits retraction of said fitting from the host vessel;
- wherein said fitting comprises a plurality of interconnected links having spaces therebetween and adapted to engage the inner surface of the host vessel wherein the area of contact between the interconnected links and the inner surface area of the host vessel is no greater than about 35% of the total area of the fitting upon forming an anastomosis.

10. The system of claim 9 wherein at least said leading and rear segments are formed from said interconnected links.

11. The system of claim 10 wherein said fitting further comprises at least one lateral portion positioned between said leading segment and said rear segment, and said at least one lateral portion is formed from said interconnected links.

12. The system of claim 11 wherein said at least one lateral portion provides a smooth transition between said leading segment and said rear segment.

13. The system of claim 9 wherein said base and said rear segment are positioned relative to each other wherein said graft is positioned at an angle with said host vessel upon operative engagement of said fitting within said graft and said host vessel.

14. The system of claim 13 wherein said angle is in the range from about 20° to about 70°.

15. The system of claim 9 wherein said leading segment has a rounded-toe configuration.

16. The system of claim 9 wherein said rear segment has an outwardly facing surface and an inwardly facing surface and further wherein at least a portion of said at least one torsion member faces said inwardly facing surface.

17. An anastomosis connector system comprising a fitting comprising:
- a base adapted for attachment to a graft,
- a leading segment extending from said base and adapted for introduction into a host vessel;
- a rear segment extending from said base, wherein said fitting has a length dimension extending from said leading segment to said rear segment and has a width dimension transverse to said length dimension, wherein said fitting has an asymmetrical configuration about said width dimension; and
- a hinge zone associated with said base and comprising at least one torsion member,
- wherein by means of said at least one torsion member said rear segment is torsionally deflectable about said hinge zone relative to said base such that said fitting can be advanced into a host vessel and wherein, upon returning to a substantially undeflected position, said rear segment prohibits retraction of said fitting from the host vessel;
- wherein said fitting comprises a plurality of interconnected links having spaces therebetween and adapted to engage the inner surface of the host vessel wherein the area of contact between the interconnected links and the inner surface area of the host vessel is no greater than about 35% of the total area of the fitting upon forming an anastomosis.

18. The system of claim 17 wherein at least said leading and rear segments are formed from said interconnected links.

19. The system of claim 18 wherein said fitting further comprises at least one lateral portion positioned between said leading segment and said rear segment, and said at least one lateral portion is formed from said interconnected links.

20. The system of claim 19 wherein said at least one lateral portion provides a smooth transition between said leading segment and said rear segment.

21. The system of claim 17 wherein said base and said rear segment are positioned relative to each other wherein said graft is positioned at an angle with said host vessel upon operative engagement of said fitting within said graft and said host vessel.

22. The system of claim 21 wherein said angle is in the range from about 20° to about 70°.

23. The system of claim 17 wherein said leading segment has a rounded-toe configuration.

24. The system of claim 17 wherein said rear segment has an outwardly facing surface and an inwardly facing surface and further wherein at least a portion of said at least one torsion member faces said inwardly facing surface.

25. An anastomosis connector system comprising a fitting comprising:
- a base adapted for attachment to a graft, wherein said base defines an ovalized opening;
- a leading segment extending from said base and adapted for introduction into a host vessel;
- a rear segment extending from said base; and
- a hinge zone associated with said base and comprising at least one torsion member,
- wherein by means of said at least one torsion member said rear segment is torsionally deflectable about said hinge zone relative to said base such that said fitting can be advanced into a host vessel and wherein, upon returning to a substantially undeflected position, said rear segment prohibits retraction of said fitting from the host vessel;
- wherein said fitting comprises a plurality of interconnected links having spaces therebetween and adapted to engage the inner surface of the host vessel wherein the area of contact between the interconnected links and the inner surface area of the host vessel is no greater than about 35% of the total area of the fitting upon forming an anastomosis.

26. The system of claim 25 wherein at least said leading and rear segments are formed from said interconnected links.

27. The system of claim 26 wherein said fitting further comprises at least one lateral portion positioned between said leading segment and said rear segment, and said at least one lateral portion is formed from said interconnected links.

28. The system of claim 27 wherein said at least one lateral portion provides a smooth transition between said leading segment and said rear segment.

29. The system of claim 25 wherein said base and said rear segment are positioned relative to each other wherein said graft is positioned at an angle with said host vessel upon operative engagement of said fitting within said graft and said host vessel.

30. The system of claim 29 wherein said angle is in the range from about 20° to about 70°.

31. The system of claim 25 wherein said leading segment has a rounded-toe configuration.

32. The system of claim 25 wherein said rear segment has an outwardly facing surface and an inwardly facing surface and further wherein at least a portion of said at least one torsion member faces said inwardly facing surface.

33. An anastomosis connector system comprising:
  a fitting comprising:
    a base adapted for attachment to a graft;
    a leading segment extending from said base and adapted for introduction into a host vessel;
    a rear segment extending from said base; and
    a hinge zone associated with said base and comprising at least one torsion member,
  wherein by means of said at least one torsion member said rear segment is torsionally deflectable about said hinge zone relative to said base such that said fitting can be advanced into a host vessel and wherein, upon returning to a substantially undeflected position, said rear segment prohibits retraction of said fitting from the host vessel;
  wherein said fitting comprises a plurality of interconnected links having spaces therebetween and adapted to engage the inner surface of the host vessel wherein the area of contact between the interconnected links and the inner surface area of the host vessel is no greater than about 35% of the total area of the fitting upon forming an anastomosis; and a collar adapted for interfacing with said fitting external to said graft.

34. The system of claim 33 wherein said fitting base comprises an opening and said collar comprises an opening wherein said fitting opening and said collar opening are complementary.

* * * * *